(12) United States Patent
Kwak et al.

(10) Patent No.: US 9,067,885 B2
(45) Date of Patent: Jun. 30, 2015

(54) ORGANIC LIGHT-EMITTING DEVICE

(75) Inventors: Yoon-Hyun Kwak, Yongin (KR);
Seok-Hwan Hwang, Yongin (KR);
Young-Kook Kim, Yongin (KR);
Hye-Jin Jung, Yongin (KR); Jong-Hyuk
Lee, Yongin (KR); Hyung-Jun Song,
Yongin (KR)

(73) Assignee: Samsung Display Co., Ltd., Yongin,
Gyeonggi-Do (KR)

( * ) Notice: Subject to any disclaimer, the term of this
patent is extended or adjusted under 35
U.S.C. 154(b) by 897 days.

(21) Appl. No.: 13/103,863

(22) Filed: May 9, 2011

(65) Prior Publication Data
US 2011/0297919 A1 Dec. 8, 2011

(30) Foreign Application Priority Data
Jun. 3, 2010 (KR) .................. 10-2010-0052349

(51) Int. Cl.
H01L 51/54 (2006.01)
C07D 209/58 (2006.01)
(Continued)

(52) U.S. Cl.
CPC ............ C07D 209/58 (2013.01); C07D 401/14
(2013.01); C07D 403/10 (2013.01);
(Continued)

(58) Field of Classification Search
CPC .. C07D 209/58; C07D 403/10; C07D 417/10;
C07D 471/04; C07D 487/04; C07D 401/14;
H05B 33/14; H01L 51/0072; H01L 51/0054;
H01L 51/0059; H01L 51/0064; H01L
51/0081; H01L 51/0085; H01L 51/0087;
H01L 51/5012; C09K 11/06; C09K
2211/1007; C09K 2211/1011; C09K
2211/1022; C09K 2211/1029; C09K
2211/1033; C09K 2211/1037; C09K
2211/1044
See application file for complete search history.

(56) References Cited

U.S. PATENT DOCUMENTS 3,904,761 A 9/1975 Novick, Jr. et al.
(Continued)

FOREIGN PATENT DOCUMENTS

CN 101053636 A 10/2007
(Continued)

OTHER PUBLICATIONS

Derwent abstract for CN 101407493 A, publication date Apr. 2009.*
(Continued)

Primary Examiner — Dawn L. Garrett
(74) Attorney, Agent, or Firm — Knobbe Martens Olson &
Bear LLP

(57) ABSTRACT

A heterocyclic compound represented by Formula 1 or Formula 2 below and an organic light-emitting device including the heterocyclic compound:

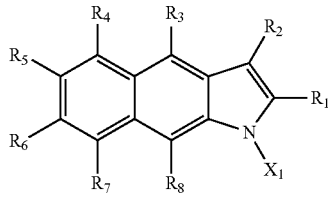

Formula 1

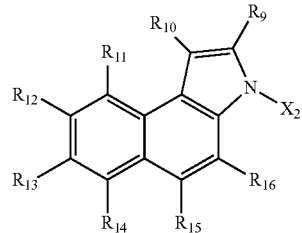

Formula 2 wherein $X_1$, $X_2$, and $R_1$ through $R_{16}$ are defined as in the specification.

34 Claims, 1 Drawing Sheet

(51) Int. Cl.

| | | |
|---|---|---|
| *C07D 401/14* | (2006.01) | |
| *C07D 403/10* | (2006.01) | |
| *C07D 417/10* | (2006.01) | |
| *C07D 471/04* | (2006.01) | |
| *C07D 487/04* | (2006.01) | |
| *C09K 11/06* | (2006.01) | |
| *H05B 33/14* | (2006.01) | |
| *H01L 51/00* | (2006.01) | |
| *H01L 51/50* | (2006.01) | |

(52) U.S. Cl.
CPC ............ *C07D417/10* (2013.01); *C07D 471/04* (2013.01); *C07D 487/04* (2013.01); *C09K 11/06* (2013.01); *C09K 2211/1007* (2013.01); *C09K 2211/1011* (2013.01); *C09K 2211/1022* (2013.01); *C09K 2211/1029* (2013.01); *C09K 2211/1033* (2013.01); *C09K 2211/1037* (2013.01); *C09K 2211/1044* (2013.01); *H01L 51/0054* (2013.01); *H01L 51/0059* (2013.01); *H01L 51/0064* (2013.01); *H01L 51/0072* (2013.01); *H01L 51/0081* (2013.01); *H01L 51/0085* (2013.01); *H01L 51/0087* (2013.01); *H01L 51/5012* (2013.01); *H05B 33/14* (2013.01)

(56) References Cited

U.S. PATENT DOCUMENTS

| | | | | |
|---|---|---|---|---|
| 5,281,489 | A * | 1/1994 | Mori et al. ................... | 428/690 |
| 5,645,948 | A | 7/1997 | Shi et al. | |
| 2004/0059130 | A1 * | 3/2004 | Beight et al. .................. | 548/427 |
| 2006/0086938 | A1 * | 4/2006 | Kang et al. ....................... | 257/72 |
| 2008/0124455 | A1 | 5/2008 | Shin et al. | |
| 2009/0054652 | A1 | 2/2009 | Yano et al. | |
| 2009/0295276 | A1 | 12/2009 | Asari et al. | |

FOREIGN PATENT DOCUMENTS

| | | | |
|---|---|---|---|
| CN | 101407493 | | 4/2009 |
| CN | 101407493 B | * | 7/2010 |
| EP | 1808433 A1 | | 7/2007 |
| EP | 2301920 A1 | | 8/2010 |
| EP | 2292602 A1 | | 9/2010 |
| EP | 2292601 A1 | | 3/2011 |
| JP | 2000-508352 A | | 7/2000 |
| JP | 2005-93159 A | | 4/2005 |
| JP | 2008-013616 A | | 1/2008 |
| JP | 2008028424 A | | 2/2008 |
| JP | 2008-133225 | | 6/2008 |
| JP | 2009-532501 A | | 9/2009 |
| JP | 2010-073987 | | 4/2010 |
| JP | 2010-513494 A | | 4/2010 |
| JP | 2011-219473 A | | 11/2011 |
| KR | 1020010015513 A | | 2/2001 |
| KR | 10-2007-0060156 A | | 6/2007 |
| KR | 10-2008-0085000 | | 9/2008 |
| KR | 10-2008-0114742 | | 12/2008 |
| WO | WO 03/059014 A1 | | 7/2003 |
| WO | WO 2006/041874 A2 | | 4/2006 |
| WO | WO 2006/041874 A2 | | 4/2006 |

OTHER PUBLICATIONS

Machine translation for CN 101407493 B (which has a publication date of Jul. 2010).*
Official Action issued by the Korean Industrial Property Office dated Feb. 28, 2012 in Korean Patent Application No. 10-2010-0052349.
Laura A. McAlliser, Rosemary A. McCormick, Karen M. James, Stephen Brand, Nigel Willetts and David J. Procter, A Fluorous, Pummerer Cyclative-Capture Strategy for the Synthesis of N-Heterocycles, European Journal, 2007, 1032-1046, vol. 13, Chemistry (A European Journal), www.chemeurj.org.
Viresh H. Rawal, Robert J. Jones and Michael P. Cava, Palladium Mediated Dehydrogenation in the Photochemical Cyclization of Hetercyclic Analogs of Stilbene, Letters, 1985, 2423-2426, vol. 26, No. 20, Pergamon Press Ltd., Great Britain.
Hiroshi Miyasaka, Takao Moriyama and Akira Itaya, Direct Detection of the Hole Migration along the Polymer Chain by Means of Picosecond Transient Absorption and Dichroism Measurements: Poly (N-vinylbenzocarbazole) Systems in 1,2-Dichloroethane Solution, Article, 1997, 10726-10732, vol. 101, J. Phys. Chem B.
J. Hodge Markgraf and Daniel E. Patterson, A Convenient Route to Heteronaphthacenes, 1996, 109-111, vol. 33, J. Heterocyclic Chem.
Transactions, Journal of the Chemical Society, 1910 vol. XCVII, Part 1, Gurney & Jackson, 10, Paternoster Row, London.
Extended European Search Report issued by the European Patent Office dated Sep. 14, 2011, in the examination of European Patent Application No. 11168157.3, 12 pages.
http://chemicalland21.com/speciallychem/NH/1%2C1%2C2-TRIMETHYL-1H-BENZ%5BE%5DINDOLE.htm.
Org. Letters (2006), 8(26), p. 5919-5922 (abstract only).
Richards, M.B., "LXXV.—Preparation of Substituted Indoles from Benzoin and Secondary Arylamines" Transactions, Journal of the Chemical Society, Jan. 1, 1910, 977-980.
Chinese Office Action dated Feb. 19, 2014, issued in connection with corresponding Chinese Patent Application No. 201110156784.3.
Journal of the Chemical Society, Transactions, 1910, vol. 97, pp. 977-980.
Organic Letters, 2006, vol. 8, No. 26, pp. 5919-5922.
Journal of Heterocyclic Chemistry, 1993, vol. 30, No. 1, pp. 217-224.
Organic Letters, 2009, vol. 11, No. 4, pp. 1007-1010.
Japanese Office Action mailed May 19, 2015, issued in corresponding Application No. JP 2011-113418.

* cited by examiner

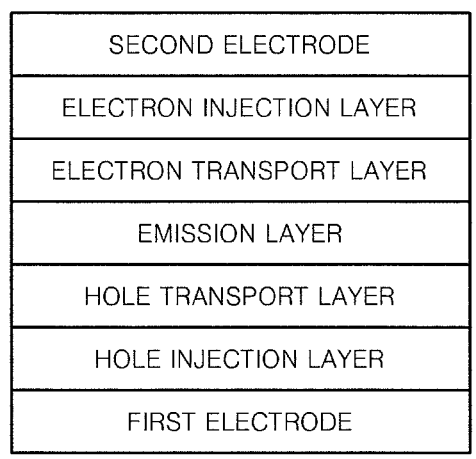

ORGANIC LIGHT-EMITTING DEVICE

CROSS-REFERENCE TO RELATED APPLICATIONS

This application claims the benefit of Korean Patent Application No. 10-2010-0052349, filed on Jun. 3, 2010, in the Korean Intellectual Property Office, the disclosure of which is incorporated herein in its entirety by reference.

BACKGROUND

1. Field

The present embodiments relate to a heterocyclic compound represented by Formula 1 or Formula 2 and an organic light-emitting device including the heterocyclic compound.

2. Description of the Related Technology

Organic light-emitting devices are self-emitting display devices and have wide viewing angles, high contrast ratios, and short response times. Due to these characteristics, organic light-emitting devices are drawing more attention.

Such organic light-emitting devices may be roughly classified into inorganic light-emitting devices that include emission layers containing inorganic compounds, and organic light-emitting devices that include emission layers containing organic compounds. Organic light-emitting devices tend to have higher luminance, lower driving voltages, and shorter response times than inorganic light-emitting devices, and can render multi-colored displays. In addition, organic light-emitting devices produce various colors. Thus, much research into such organic light-emitting devices has been conducted.

Typically, an organic light-emitting device has a stack structure including an anode, a cathode and an organic emission layer between the anode and the cathode. However, a hole injection layer and/or a hole transport layer may be further stacked between the anode and the organic emission layer, and/or an electron transport layer may be further stacked between the organic emission layer and the cathode. An organic light-emitting device may have an anode/hole transport layer/organic emission layer/cathode structure or an anode/hole transport layer/organic emission layer/electron transport layer/cathode structure.

As the material for forming the organic emission layer, naphthalene derivatives may be used. However, organic light-emitting devices including such materials do not have satisfactory life span, efficiency, and power consumption characteristics, thereby improvement in this regard is still necessary.

SUMMARY

Some of the present embodiments relate to heterocyclic compound represented by Formula 1 below:

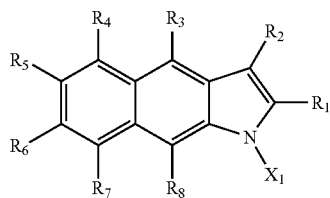

Formula 1 wherein $X_1$ is a substituted or unsubstituted $C_1$-$C_{50}$ alkyl group, a substituted or unsubstituted $C_3$-$C_{50}$ cycloalkyl group, a substituted or unsubstituted $C_5$-$C_{50}$ arylthio group, a substituted or unsubstituted $C_5$-$C_{60}$ aryl group, a substituted amino group with a $C_5$-$C_{60}$ aryl group, a substituted or unsubstituted $C_3$-$C_{60}$ heteroaryl group, or a substituted or unsubstituted $C_6$-$C_{60}$ condensed polycyclic group; and $R_1$ through $R_8$ are each independently a hydrogen atom, a heavy hydrogen atom, a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a substituted or unsubstituted $C_5$-$C_{60}$ aryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group, wherein two neighboring substituents among $R_1$ through $R_8$ may link to each other to form an aromatic ring.

A heterocyclic compound represented by Formula 2 below:

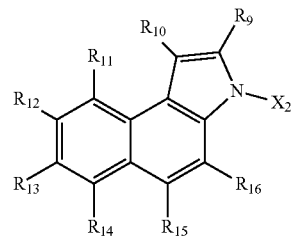

Formula 2 wherein $X_2$ is a substituted or unsubstituted $C_1$-$C_{50}$ alkyl group, a substituted or unsubstituted $C_3$-$C_{50}$ cycloalkyl group, a substituted or unsubstituted $C_5$-$C_{50}$ arylthio group, a substituted or unsubstituted $C_5$-$C_{60}$ aryl group, a substituted amino group with a $C_5$-$C_{60}$ aryl group, a substituted or unsubstituted $C_3$-$C_{60}$ heteroaryl group, or a substituted or unsubstituted $C_6$-$C_{60}$ condensed polycyclic group; and $R_9$ through $R_{16}$ are each independently a hydrogen atom, a heavy hydrogen atom, a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a substituted or unsubstituted $C_5$-$C_{60}$ aryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group, wherein two neighboring substituents among $R_9$ through $R_{16}$ may link to each other to form an aromatic ring.

In some embodiments, at least one of $R_1$, $R_2$, $R_5$, $R_9$, $R_{10}$ or $R_{13}$ is an aryl group.

In some embodiments, at least one of $R_1$, $R_2$, $R_5$, $R_9$, $R_{10}$ or $R_{13}$ is a unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a unsubstituted $C_5$-$C_{50}$ arylamine group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group or a halogen group; a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group or a halogen group; or a substituted $C_5$-$C_{50}$ arylamine group which is substituted with a $C_1$-$C_5$ alkyl group, a $C_1$-$C_5$ alkoxy group, a cyano group, an amine group, a phenoxy group, a phenyl group and a halogen group.

In some embodiments, $X_1$ is a unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group, a halogen group, or a $C_3$-$C_{60}$ heteroaryl group; or a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group, a halogen group or a $C_3$-$C_{10}$ heteroaryl group.

In some embodiments, $X_2$ is a unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group, a halogen group, or a $C_3$-$C_{10}$ heteroaryl group; or a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group, a halogen group or a $C_3$-$C_{10}$ heteroaryl group.

In some embodiments, $R_1$, $R_2$, $R_9$ and $R_{10}$ are each independently a methyl group or a phenyl group.

In some embodiments, $R_1$, $R_2$, $R_9$ and $R_{10}$ are each independently a methyl group or a phenyl group.

Some embodiments relate to one of the compounds below:

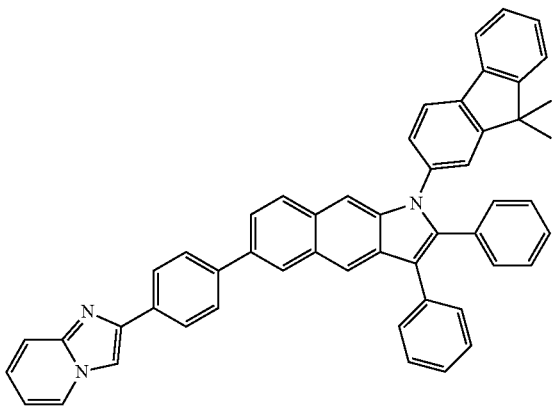

17

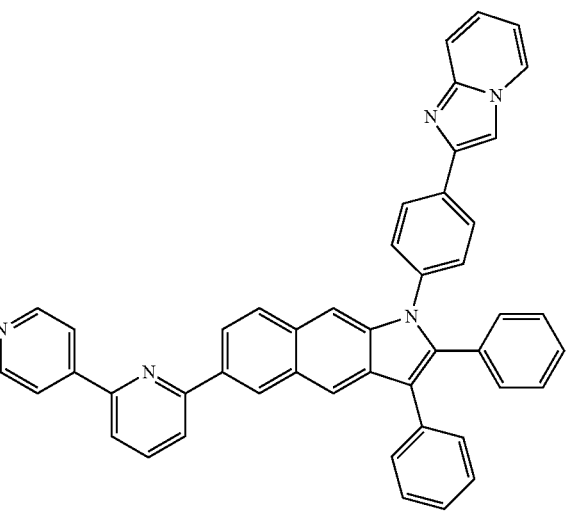

27

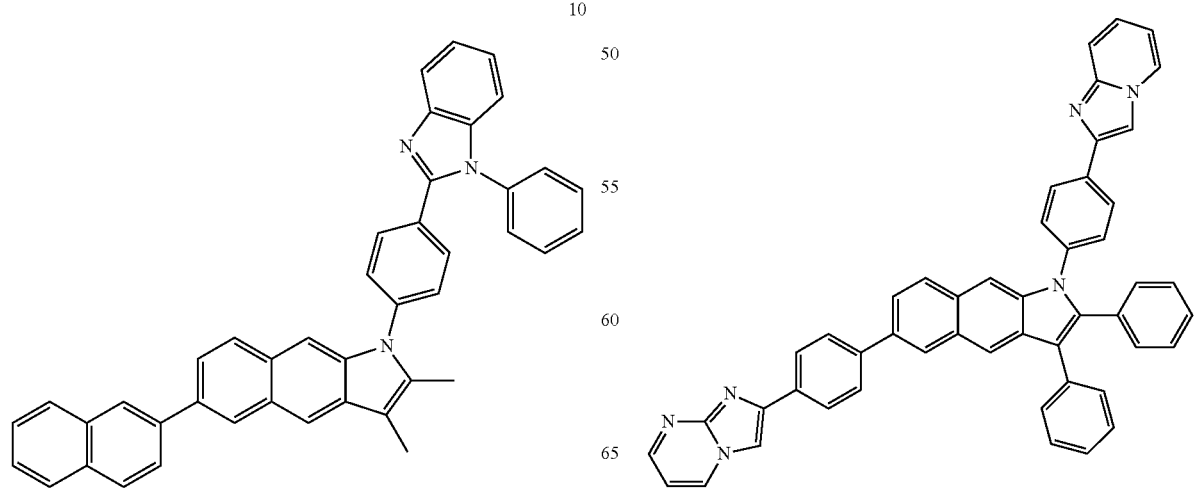

10

33

23

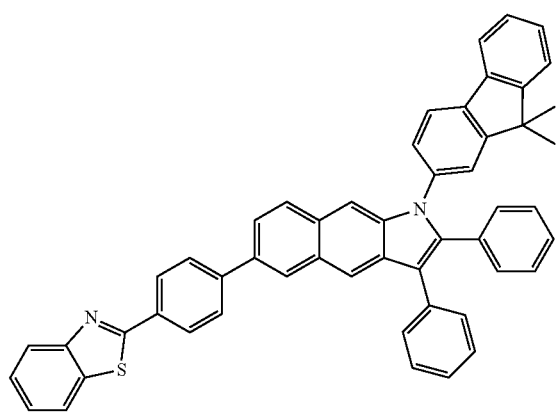

Some embodiments relate to one of the compounds below:

42

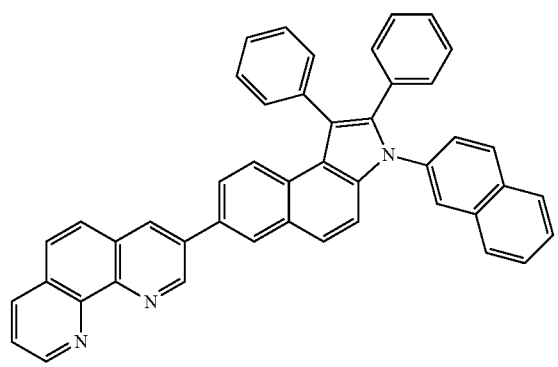

38

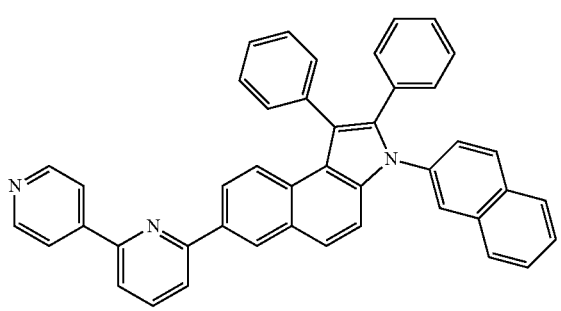

40

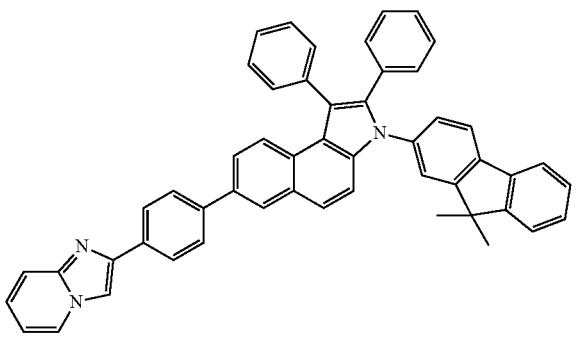

45

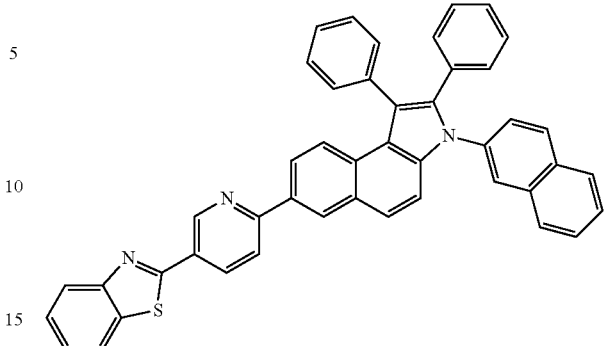

52

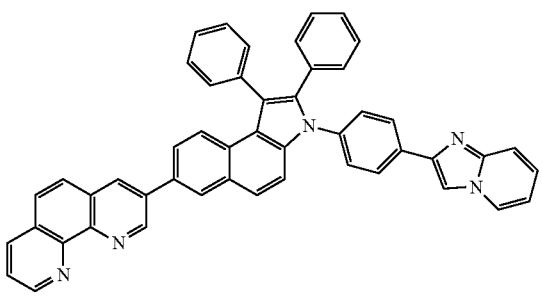

52

Some embodiments relate to an organic light-emitting device comprising:
a first electrode;
a second electrode; and
an organic layer between the first electrode and the second electrode,
the organic layer comprises a first layer including the heterocyclic compound of claim 1.

An organic light-emitting device comprising:
a first electrode;
a second electrode; and
an organic layer between the first electrode and the second electrode,
the organic layer comprises a first layer including the heterocyclic compound of claim 2.

In some embodiments, the first layer comprises an electron injection layer, an electron transport layer a single film having both an electron injection function and an electron transport function, or an emission layer.

In some embodiments, the first layer comprises an electron injection layer, an electron transport layer a single film having both an electron injection function and an electron transport function, or an emission layer.

In some embodiments, the first layer comprises an emission layer, and the heterocyclic compound is used as a host or dopant for a fluorescent or phosphorescent device.

In some embodiments, the first layer comprises an emission layer, and the heterocyclic compound is used as a host or dopant for a fluorescent or phosphorescent device.

In some embodiments, the first layer comprises an emission layer, an electron injection layer or an electron transport layer, and the emission layer comprises an anthracene compound, an arylamine compound, or a styryl compound.

In some embodiments, the first layer comprises an emission layer, an electron injection layer or an electron transport layer, and the emission layer comprises an anthracene compound, an arylamine compound, or a styryl compound.

In some embodiments, the first layer comprises an emission layer, an electron injection layer or an electron transport layer, and the emission layer comprises a red emission layer, a green emission layer, a blue emission layer or a white emission layer that comprises a phosphorescent compound.

In some embodiments, the first layer comprises an emission layer, an electron injection layer or an electron transport layer, and the emission layer comprises a red emission layer, a green emission layer, a blue emission layer or a white emission layer that comprises a phosphorescent compound.

In some embodiments, the organic layer further comprises at least one layer selected from the group consisting of a hole injection layer, a hole transport layer, a functional layer having both hole injection and transport functions, an electron blocking layer, an emission layer, a hole blocking layer, an electron transport layer, an electron injection layer and a combination of at least two of these layers.

In some embodiments, at least one of the hole injection layer, the hole transport layer, and the functional layer having both hole injection and transport functions further comprises a charge-generating material.

In some embodiments, the electron transport layer comprises an electron transporting organic material and a metal-containing material.

In some embodiments, the metal-containing material comprises a lithium complex.

In some embodiments, the organic layer further comprises at least one layer selected from the group consisting of a hole injection layer, a hole transport layer, a functional layer having both hole injection and transport functions, an electron blocking layer, an emission layer, a hole blocking layer, an electron transport layer, an electron injection layer and a combination of at least two of these layers.

In some embodiments, at least one of the hole injection layer, the hole transport layer, and the functional layer having both hole injection and transport functions further comprises a charge-generating material.

In some embodiments, the electron transport layer comprises an electron transporting organic material and a metal-containing material.

In some embodiments, the metal-containing material comprises a lithium complex.

Some embodiments relate to an organic light-emitting device having a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport structure layer/electron injection layer/second electrode structure.

Some embodiments relate to an organic light-emitting device having a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport structure layer/electron injection layer/second electrode structure.

Some embodiments relate to an organic light-emitting device comprising:
a first electrode;
a second electrode; and
an organic layer between the first electrode and the second electrode, wherein the organic layer comprises at least one layer comprising the heterocyclic compound of claim 1, the at least one layer being formed using a wet process.

An organic light-emitting device comprising:
a first electrode;
a second electrode; and
an organic layer between the first electrode and the second electrode, wherein the organic layer comprises at least one layer comprising the heterocyclic compound of claim 2, the at least one layer being formed using a wet process.

Some embodiments relate to a flat panel display device comprising the organic light-emitting device of claim 11, wherein the first electrode of the organic light-emitting device is electrically connected to a source electrode or a drain electrode of a thin-film transistor.

Some embodiments relate to a flat panel display device comprising the organic light-emitting device of claim 12, wherein the first electrode of the organic light-emitting device is electrically connected to a source electrode or a drain electrode of a thin-film transistor.

BRIEF DESCRIPTION OF THE DRAWING

The above and other features and advantages of the present embodiments will become more apparent by describing in detail example embodiments thereof with reference to the attached drawing in which:

FIG. 1 is a diagram of the structure of an organic light-emitting device according to an embodiment.

DETAILED DESCRIPTION

The present embodiments will now be described more fully with reference to the accompanying drawings, in which example embodiments of the embodiments are shown.

A heterocyclic compound according to an embodiment is represented by Formula 1 below:

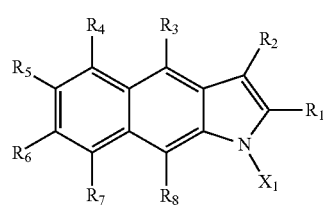

Formula 1 wherein $X_1$ may be a substituted or unsubstituted $C_1$-$C_{50}$ alkyl group, a substituted or unsubstituted $C_3$-$C_{50}$ cycloalkyl group, a substituted or unsubstituted $C_5$-$C_{50}$ arylthio group, a substituted or unsubstituted $C_5$-$C_{60}$ aryl group, a substituted amino group with a $C_5$-$C_{60}$ aryl group, a substituted or unsubstituted $C_3$-$C_{60}$ heteroaryl group, or a substituted or unsubstituted $C_6$-$C_{60}$ condensed polycyclic group; and $R_1$ through $R_8$ may each independently be a hydrogen atom, a heavy hydrogen atom, a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a substituted or unsubstituted $C_5$-$C_{60}$ aryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group, wherein two neighboring substituents among $R_1$ through $R_8$ may link to each other to form an aromatic ring.

A heterocyclic compound according to another embodiment is represented by Formula 2 below:

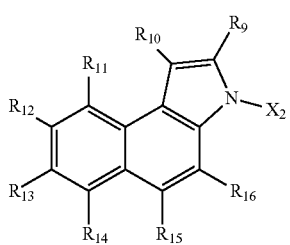

Formula 2 wherein $X_2$ may be a substituted or unsubstituted $C_1$-$C_{50}$ alkyl group, a substituted or unsubstituted $C_3$-$C_{50}$ cycloalkyl group, a substituted or unsubstituted $C_5$-$C_{50}$ arylthio group, a substituted or unsubstituted $C_5$-$C_{60}$ aryl group, a substituted amino group with a $C_5$-$C_{60}$ aryl group, a substituted or unsubstituted $C_3$-$C_{60}$ heteroaryl group, or a substituted or unsubstituted $C_6$-$C_{60}$ condensed polycyclic group; and $R_9$ through $R_{16}$ may each be independently a hydrogen atom, a heavy hydrogen atom, a substituted or unsubstituted alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a substituted or unsubstituted $C_5$-$C_{60}$ aryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group, wherein two neighboring substituents among $R_9$ through $R_{16}$ may link to each other to form an aromatic ring.

Examples of materials for forming an emission layer or an electron transport layer, which constitute an organic light-emitting device, include, but are not limited to, Alq3, 2,2',2"-(1,3,5-phenylene)tris-(1-phenyl)-1H-benzimidazol (TPBI), 2-Biphenyl-4-yl-5-(4-tert-butyl-phenyl)-[1,3,4]oxadiazole (PBD), perfluorinated chemical (PF-6P), and 2,5-bis(6'-(2', 2"-bipyridyl))-1,1-dimethyl-3,4-diphenylsiylol (Py-PySPyPy).

The heterocyclic compound of Formula 1 or Formula 2, in which a naphthalene group and an indole group are fused, has a high glass transition temperature (Tg) or a high melting point due to the inclusion of the heterocyclic moiety. Thus, the heterocyclic compound has high heat resistance against heat generated in an organic layer, between organic layers, or between an organic layer and a metal electrode when light emission occurs, and has high durability in high-temperature environments. An organic light-emitting device manufactured using the heterocyclic compound of Formula 1 or Formula 2 has good durability when stored or operated. In addition, due to the inclusion of a substituent such as a fluorene group, molecular layers formed as thin films may be maintained in good condition, thereby improving the characteristics of the organic light-emitting device.

Substituents in the heterocyclic compounds of Formulae 1 and 2 will now be described in detail.

In Formulae 1 and 2, at least one of $R_1$, $R_2$, $R_5$, $R_9$, $R_{10}$ or $R_{13}$ may be an aryl group, which may be substituted with a substituent such as those that will be described later in conjunction with a $C_1$-$C_{50}$ alkyl group. For example, at least one of $R_1$, $R_2$, $R_5$, $R_9$, $R_{10}$ or $R_{13}$ may be a unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a $C_5$-$C_{50}$ arylamine group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group or a halogen group; a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group or a halogen group; or a substituted $C_5$-$C_{50}$ arylamine group which is substituted with a $C_1$-$C_5$ alkyl group, a $C_1$-$C_5$ alkoxy group, a cyano group, an amine group, a phenoxy group, a phenyl group or a halogen group.

$X_1$ or $X_2$ may be a unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group, a halogen group, or a $C_3$-$C_{10}$ heteroaryl group; or a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group, a halogen group or a $C_3$-$C_{10}$ heteroaryl group.

$R_1$, $R_2$, $R_9$ and $R_{10}$ may each be independently a methyl group or a phenyl group.

Hereinafter, substituents described with reference to Formulae 1-2 will now be described in detail. In this regard, the numbers of carbons in substituents are presented only for illustrative purposes and do not limit the characteristics of the substituents The unsubstituted $C_1$-$C_{50}$ alkyl group used herein may be linear or branched. Examples of the unsubstituted $C_1$-$C_{50}$ alkyl group include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_3$-$C_{16}$ heteroaryl group.

The substituted $C_3$-$C_{50}$ cycloalkyl group used herein refers to a $C_3$-$C_{50}$ cyclic alkyl group wherein at least one hydrogen atom in the cycloalkyl group may be substituted with a substituent such as those described above in connection with the $C_1$-$C_{50}$ alkyl group.

The unsubstituted $C_1$-$C_{50}$ alkoxy group used herein is a group having a structure of —OA wherein A is an unsubstituted $C_1$-$C_{50}$ alkyl group as described above. Examples of the unsubstituted $C_1$-$C_{50}$ alkoxy group include, but are not limited to, a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted $C_5$-$C_{60}$ aryl group used herein refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with substituent such as those described above in conjunction with the $C_1$-$C_{50}$ alkyl group.

Examples of the substituted or unsubstituted $C_5$-$C_{60}$ aryl group include, but are not limited to, a phenyl group, a $C_1$-$C_{10}$ alkylphenyl group (for example, an ethylphenyl group), a halophenyl group (for example, o-, m-, and p-fluorophenyl group, a dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, a fluoronaphthyl group), a $C_1$-$C_{10}$ alkylnaphthyl group (for example, a methylnaphthyl group), a $C_1$-$C_{10}$ alkoxynaphthyl group (for example, a methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_3$-$C_{60}$ heteroaryl group used herein includes one, two or three heteroatoms selected from N, O, P and S. At least two rings may be fused to each other or linked to each other by a single bond. Examples of the unsubstituted $C_3$-$C_{60}$ heteroaryl group may include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, and an isoquinolinyl group. At least one hydrogen atom in the heteroaryl group may be substituted with a substituent such as those described above in conjunction with the $C_1$-$C_{50}$ alkyl group.

The unsubstituted $C_5$-$C_{50}$ aryloxy group is represented by —$OA_1$ wherein $A_1$ may be a $C_5$-$C_{50}$ aryl group. Examples of the aryloxy group may include a phenoxy group. At least one hydrogen atom in the aryloxy group may be substituted with a substituent such as those described above in conjunction with the $C_1$-$C_{50}$ alkyl group.

The unsubstituted $C_5$-$C_{50}$ arylthio group is represented by —$SA_1$ where $A_1$ may be a $C_5$-$C_{50}$ aryl group. Examples of the arylthio group include, but are not limited to, a benzenethio group, and a naphthylthio group. In the arylthio group, at least one hydrogen atom may be substituted with a substituent such as those described above in conjunction with the unsubstituted $C_1$-$C_{50}$ alkyl group.

The unsubstituted $C_6$-$C_{60}$ condensed polycyclic group used herein refers to a substituent including at least two rings wherein at least one aromatic ring and/or at least one non-aromatic ring are fused to each other.

The $C_5$-$C_{50}$ arylamine group refers to an amine group with a $C_5$-$C_{50}$ aryl group as a substituent, and the substituted $C_5$-$C_{50}$ arylamine group refers to a $C_5$-$C_{50}$ arylamine group with a substituent in the substituent aryl group.

Examples of the heterocyclic compound represented by Formula 1 or Formula 2 may include Compounds 1 through 52 presented below. However, the compounds represented by Formula 1 or Formula 2 are not limited thereto.

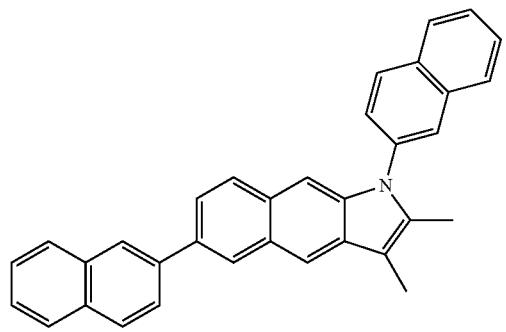

1

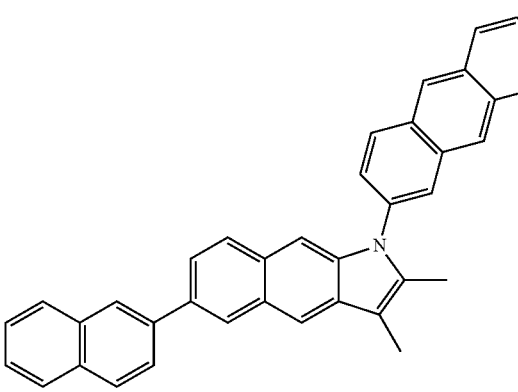

2

3
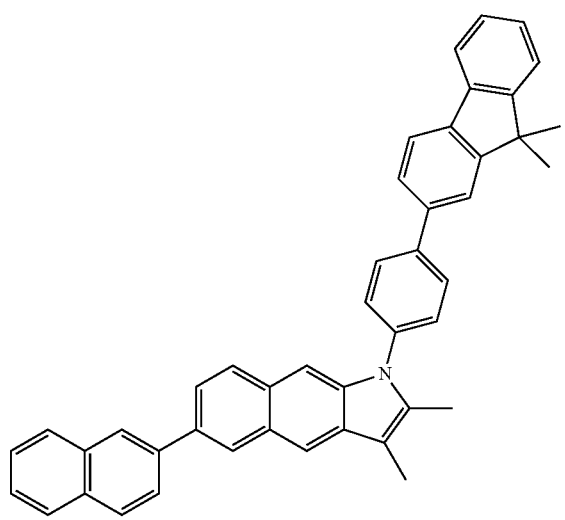
4
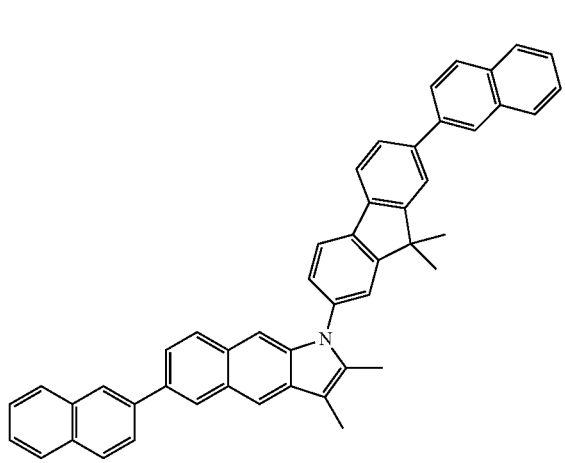
5
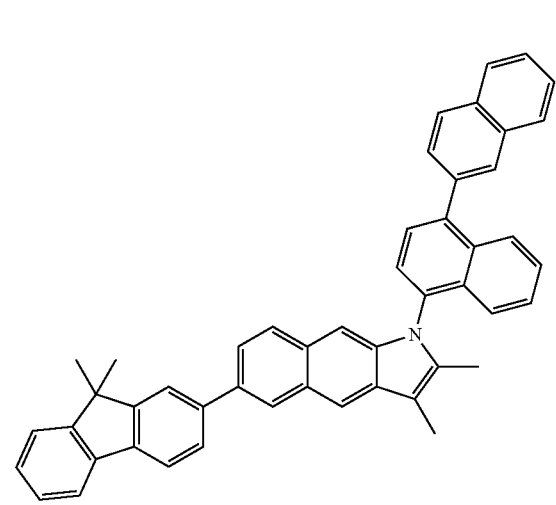
6
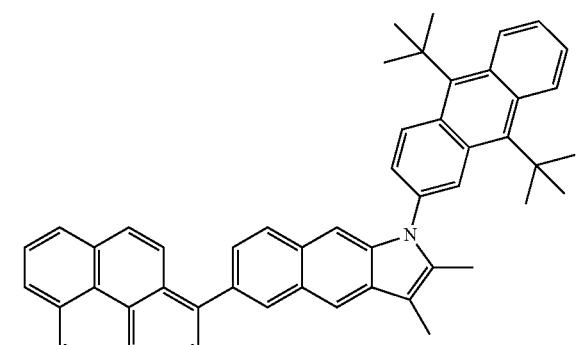
7
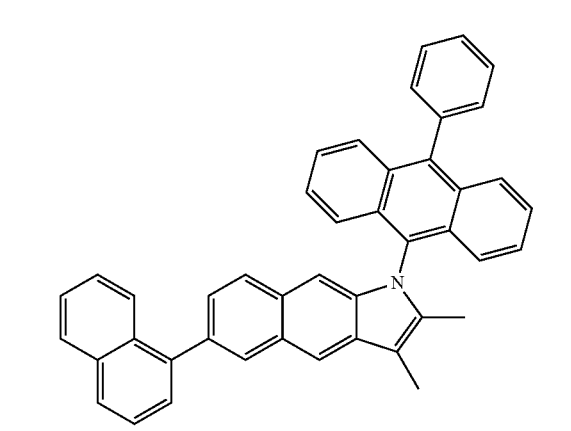
8

9
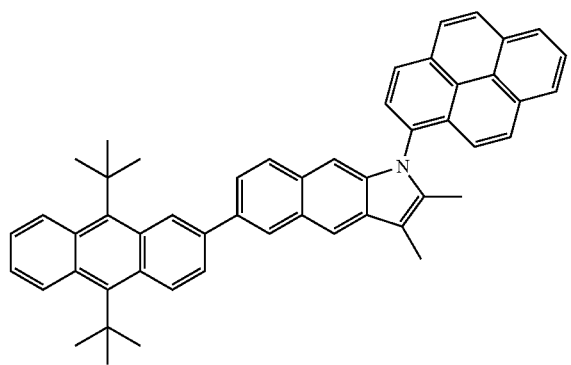
10
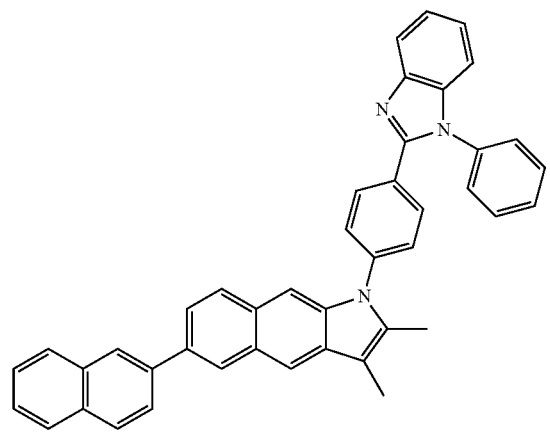
11
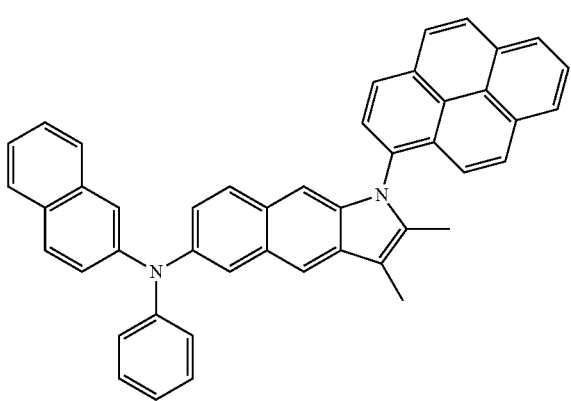
12
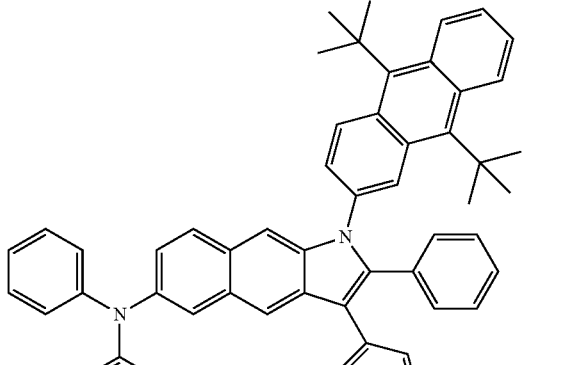
13
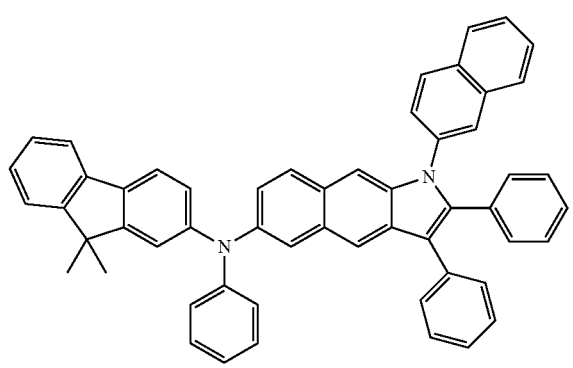
14
15
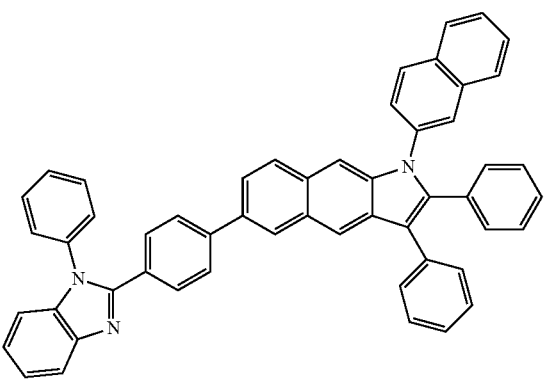

16
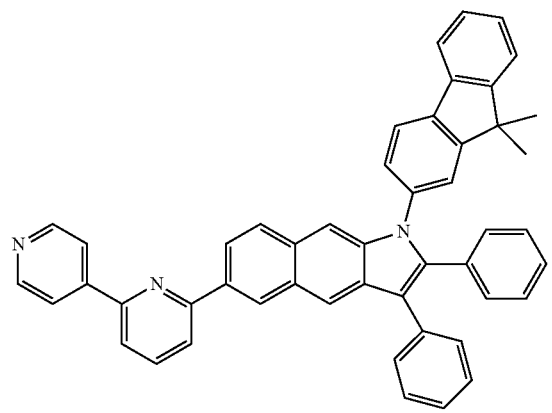
17
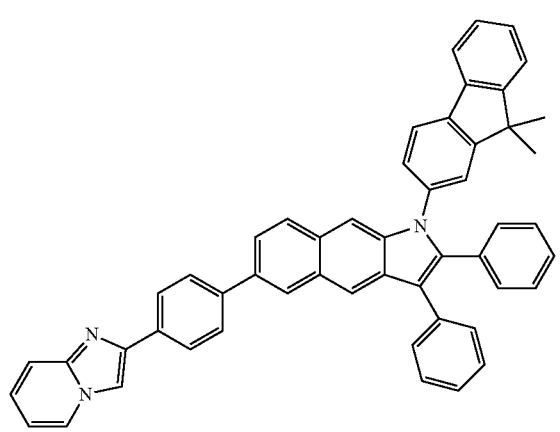
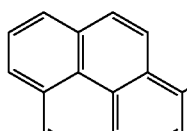
18
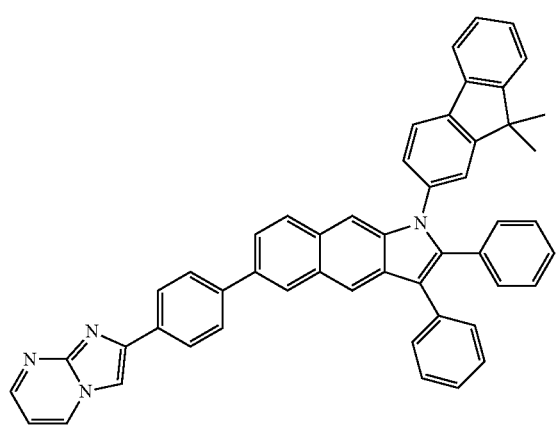
19
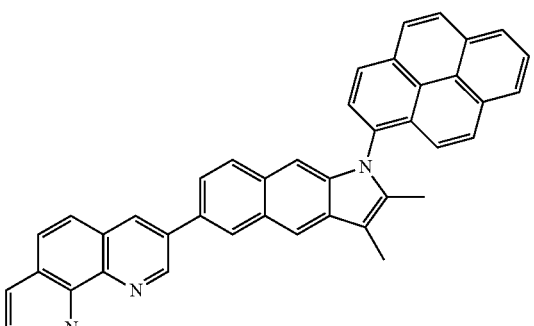
20
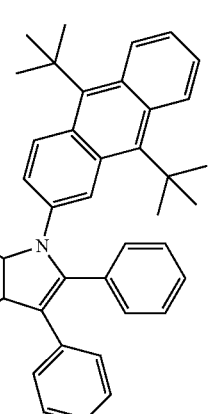
21
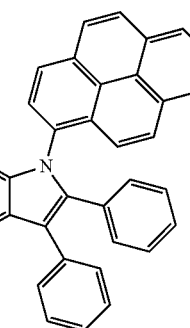
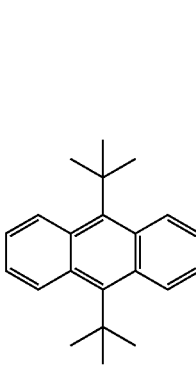

22
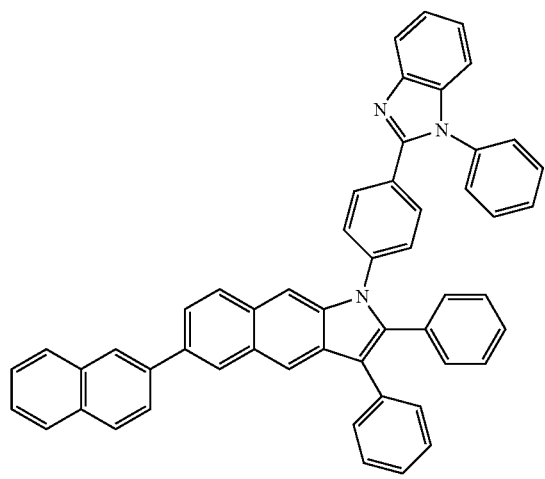
23
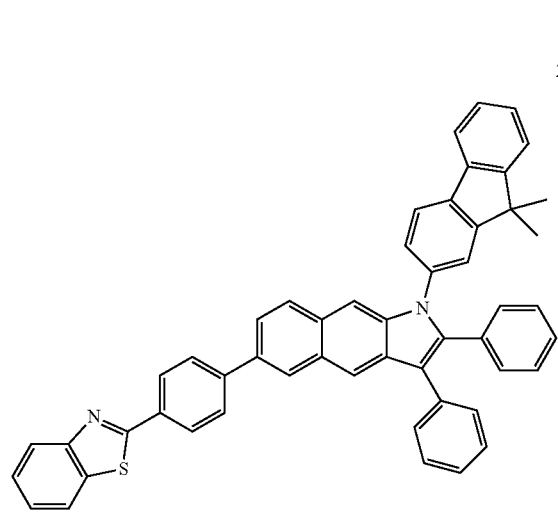
24
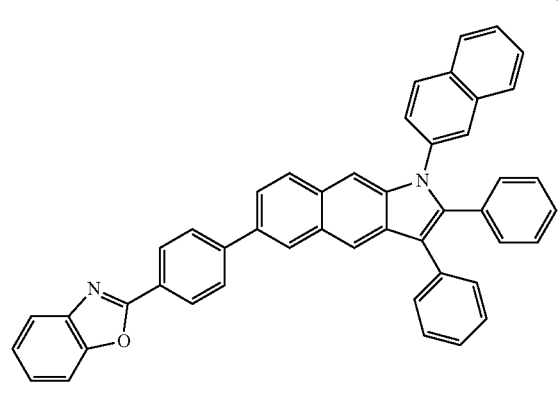
25
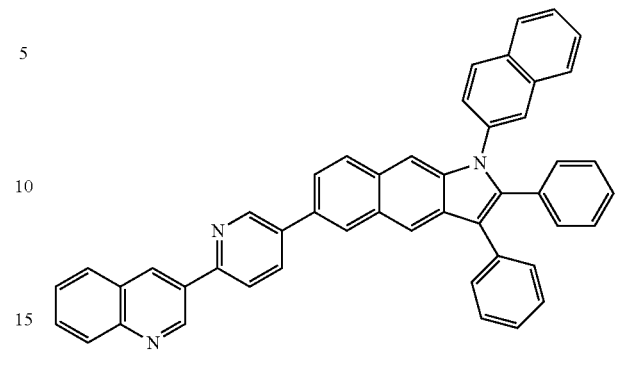
26
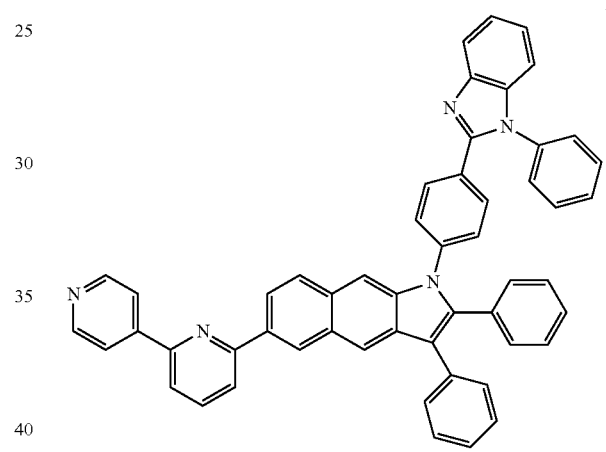
27

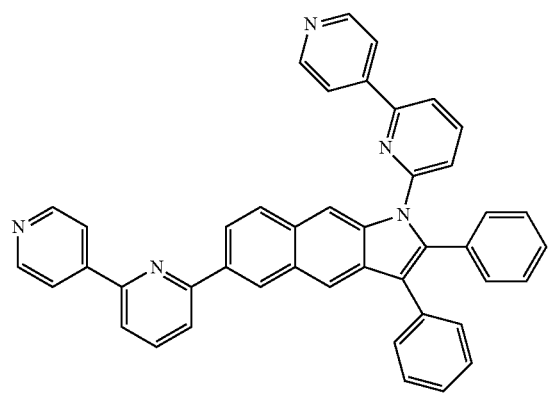
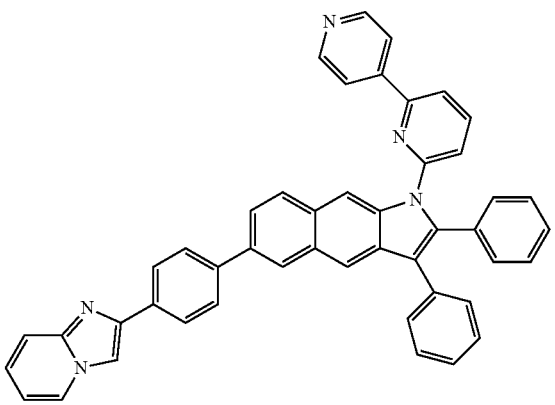
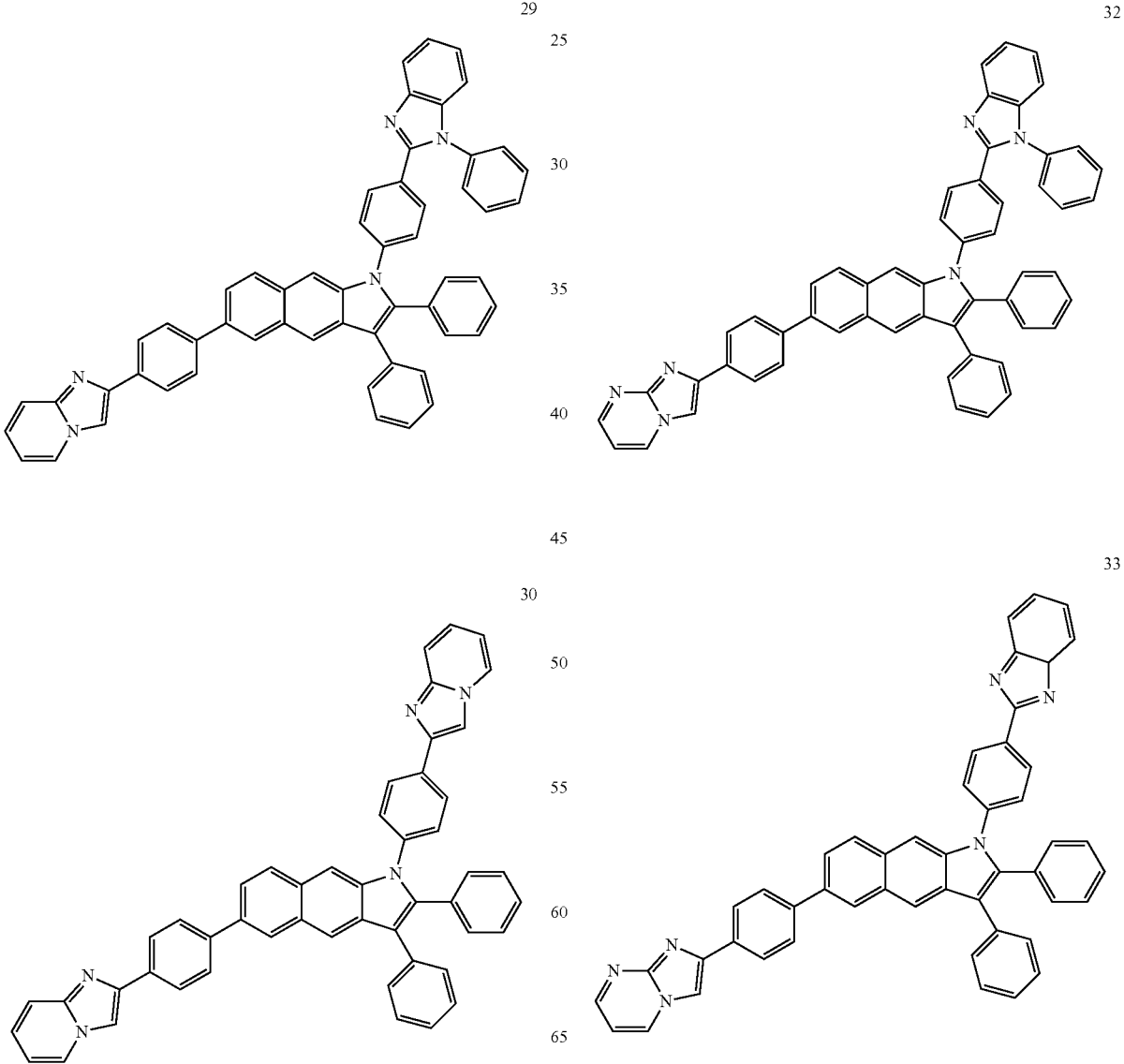

34
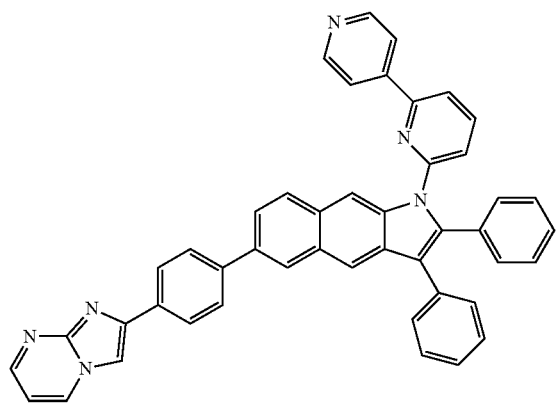
35
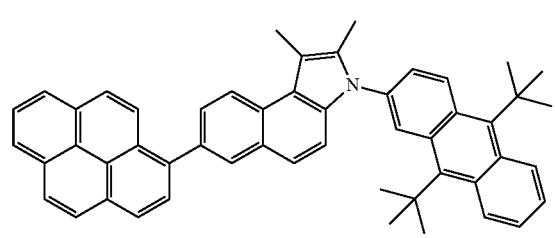
36
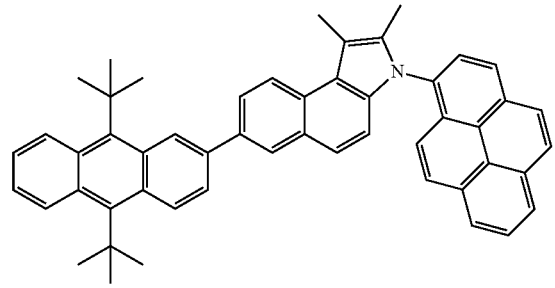
37
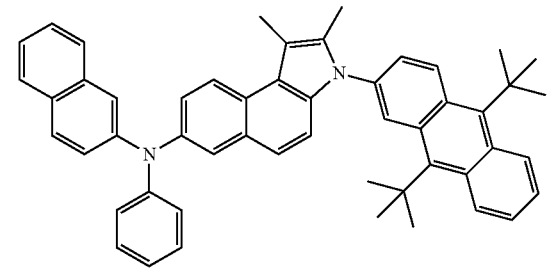
38
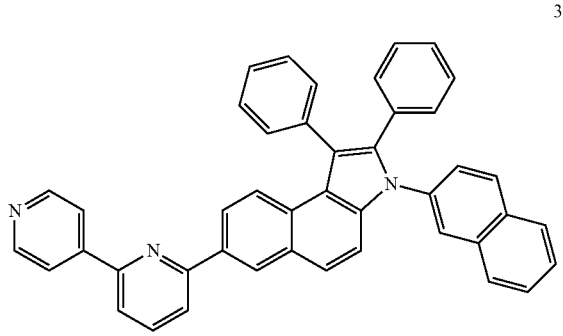
39
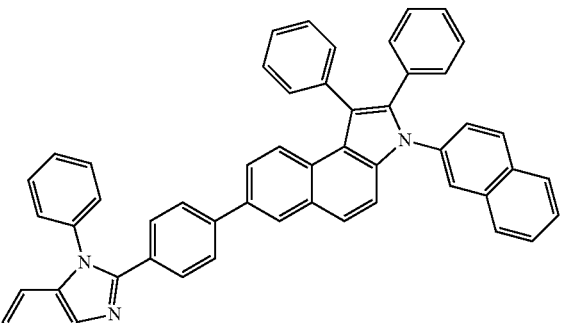
40
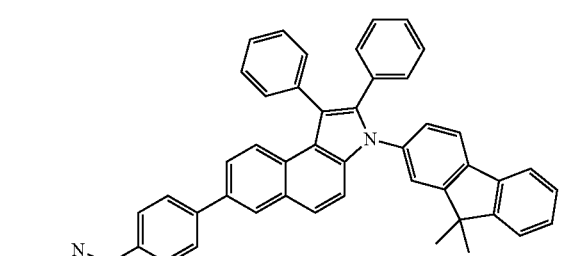
41
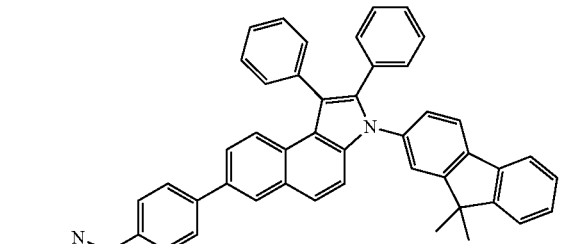
42
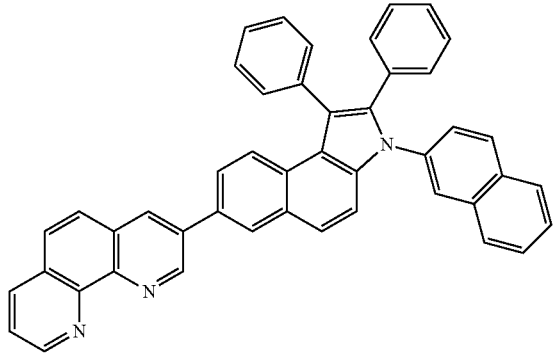

43
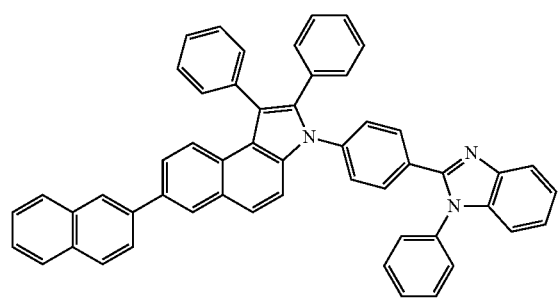
44
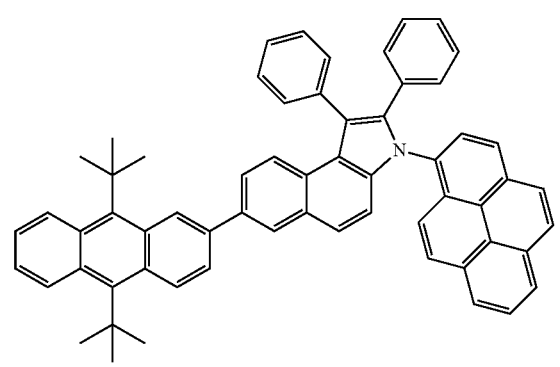
45
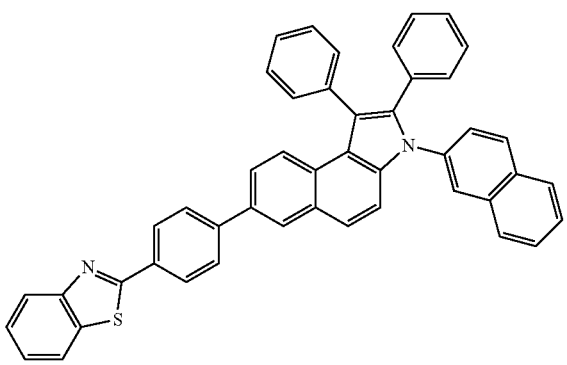
46
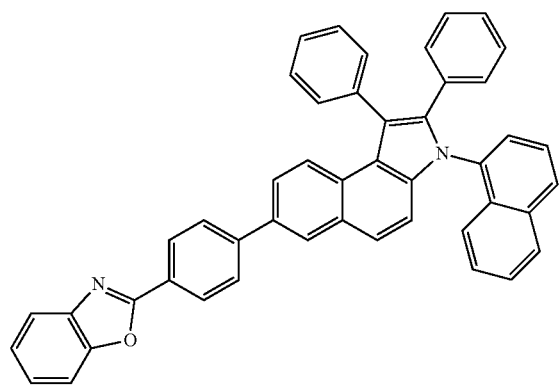
47
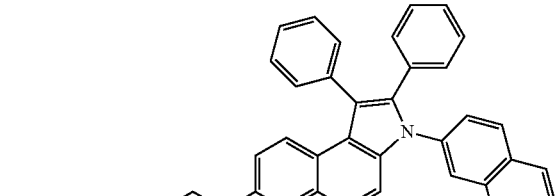
48
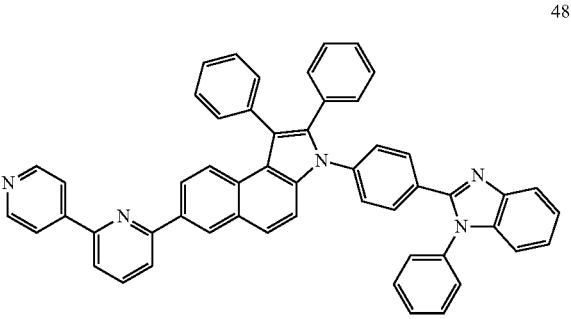
49
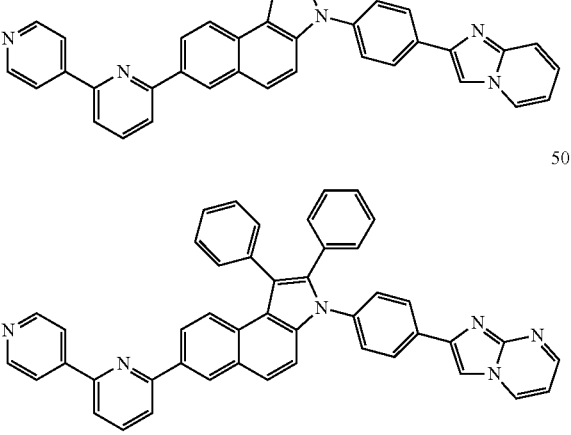
50
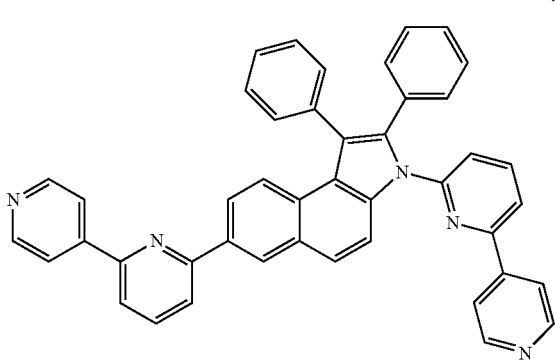

-continued

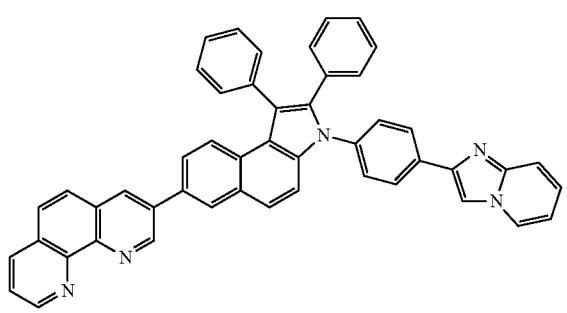

52

An organic light-emitting device according to an embodiment includes a first electrode, a second electrode, and an organic layer between the first electrode and the second electrode, wherein the organic layer includes the heterocyclic compound of Formula 1 or Formula 2 described above.

The organic layer, which includes the heterocyclic compound of Formula 1 or Formula 2, may be an electron injection layer; an electron transport layer, or a single layer having both the abilities to inject and transport electrons. Furthermore, the organic layer, which includes the heterocyclic compound of Formula 1 or 2, may be an emission layer. When the organic layer, which includes the heterocyclic compound of Formula 1 or Formula 2, is an emission layer, the heterocyclic compound of Formula 1 or Formula 2 may be used as a fluorescent or phosphorescent host, or a fluorescent dopant.

In the organic light-emitting device, when the emission layer, the electron injection layer or the electron transport layer includes the heterocyclic compound of Formula 1 or Formula 2, the emission layer may include an anthracene compound, an arylamine compound or a styryl compound, wherein the anthracene compound, the arylamine compound or the styryl compound may be unsubstituted or substituted with a substituent such as those described above in conjunction with the $C_1$-$C_{50}$ alkyl group.

In the organic light-emitting device, when the emission layer, the electron injection layer or the electron transport layer includes the heterocyclic compound of Formula 1 or Formula 2, a red emission layer, a green emission layer, a blue emission layer or a white emission layer of the emission layer may include a phosphorescent compound.

In some embodiments, the organic layer of the organic light-emitting device may further include, but is not limited to, a hole injection layer, a hole transport layer, a functional layer having both hole injection and transport functions, an emission layer, a hole blocking layer, an electron transport layer, an electron injection layer, of a combination of at least two of these layers. At least one of the hole injection layer, the hole transport layer, and the functional layer having both hole injection and transport functions, may further include, in addition to the heterocylic compound of Formula 1 and widely-known hole injection and transport materials, a charge-generating material for improving conductivity of the layer.

The charge-generating material may include, for example, a p-dopant. Nonlimiting examples of the p-dopant include quinine derivatives, including tetracyanoquinondimethane (TCNQ) and 2,3,5,6-tetrafluoro-tetracyano-1,4-benzoquinonedimethane (F4TCNQ); metal oxides, including tungsten oxide and molybdenium oxide; and cyano group-containing compounds, including a compound represented by Formula 100 below.

Formula 100

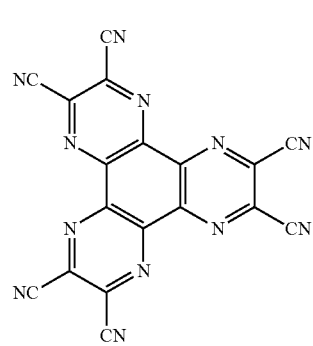

In some embodiments, when the hole injection layer, the hole transport layer, or the functional layer having both hole injection and transport functions further includes the charge-generating material, the charge-generating material may be uniformly or nonuniformly distributed in the layer.

In one embodiment, the electron transport layer of the organic light-emitting device may include an electron transporting organic compound and a metal-containing material. Nonlimiting examples of the electron transporting organic compound include ADN(9,10-di(naphthalene-2-yl)anthracene); and anthracene-based compounds, including a compound of Formula 101 and a compound of Formula 102 below.

Formula 101

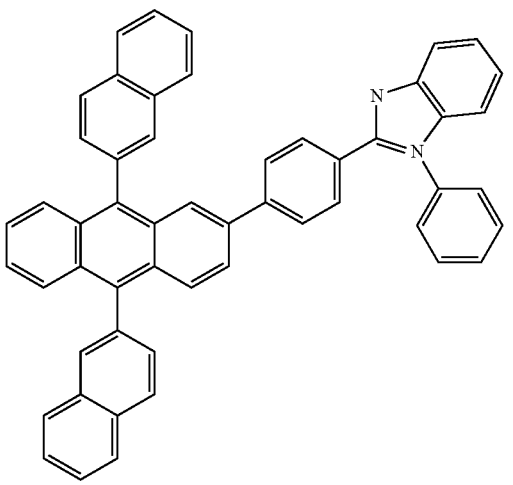

-continued

Formula 102

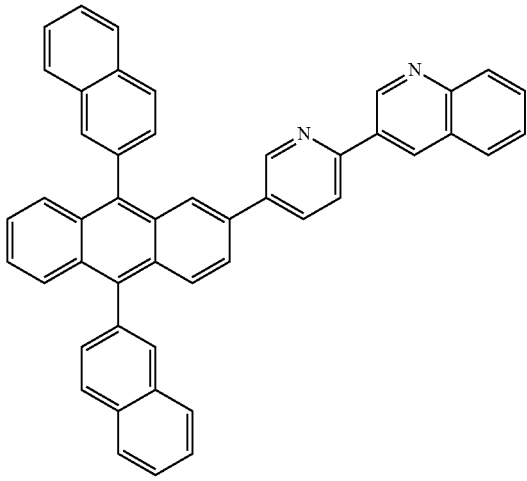

The metal-containing material may include a Li complex. Nonlimiting examples of the Li complex include lithium quinolate (LiQ) and a compound of Formula 103 below.

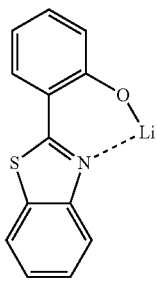

The first electrode may be an anode, and the second electrode may be a cathode, but the reverse is also possible.

In the organic light-emitting described above, the organic layer may further include at least one layer selected from the group consisting of a hole injection layer, a hole transport layer, an electron blocking layer, an emission layer, a hole blocking layer, an electron transport layer and an electron injection layer, if required.

For example, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. Alternatively, the organic light-emitting device may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure.

According to some embodiments, the organic light-emitting device may be either a top-emission organic light-emitting device or a bottom-emission organic light-emitting device.

Hereinafter, a method of manufacturing an organic light-emitting device according to an embodiment will be described with reference to FIG. 1. FIG. 1 illustrates the structure of an organic light-emitting device according to an embodiment. Referring to FIG. 1, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

The first electrode is formed on the substrate by using a deposition or sputtering method. The first electrode may comprise a first electrode material having a high work function. The first electrode may constitute an anode or a cathode. The substrate may be a substrate conventionally used in organic light-emitting devices, and may include, for example, a glass substrate or a transparent plastic substrate with excellent mechanical strength, thermal stability, transparency, surface smoothness, ease of handling, and water resistance. Examples of the first electrode material include materials, such as indium tin oxide (ITO), indium zinc oxide (IZO), tin oxide ($SnO_2$), zinc oxide (ZnO), aluminum (Al), silver (Ag), and magnesium (Mg), which have excellent conductivity. The first electrode may be formed as a transparent or reflective electrode.

Next, the HIL may be formed on the first electrode using various methods, for example, vacuum deposition, spin coating, casting, Langmuir-Blodgett (LB) deposition, or the like.

When the HIL is formed using vacuum deposition, the deposition conditions may vary according to the material used to form the HIL, and the structure and thermal characteristics of the HIL. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the material used to form the HIL, and the structure and thermal properties of the HIL. For example, the coating conditions may include a coating rate of about 2000 rpm to about 5000 rpm, and a thermal treatment temperature of about 80° C. to about 200° C., wherein the thermal treatment serves to remove the solvent after coating.

The HIL may comprise any material that is commonly used to form a HIL. Examples of the material that can be used to form the HIL include a phthalocyanine compound such as copperphthalocyanine, 4,4',4"-tris (3-methylphenylphenylamino) triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS), but are not limited thereto.

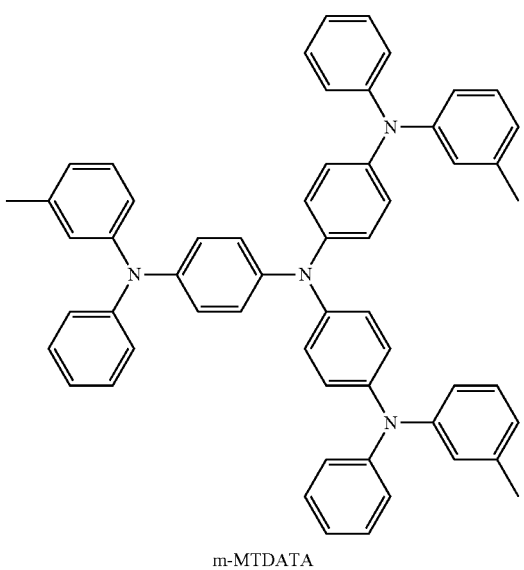

m-MTDATA

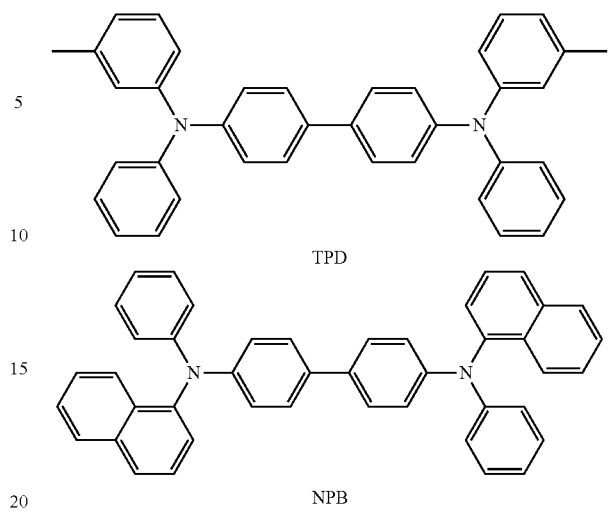

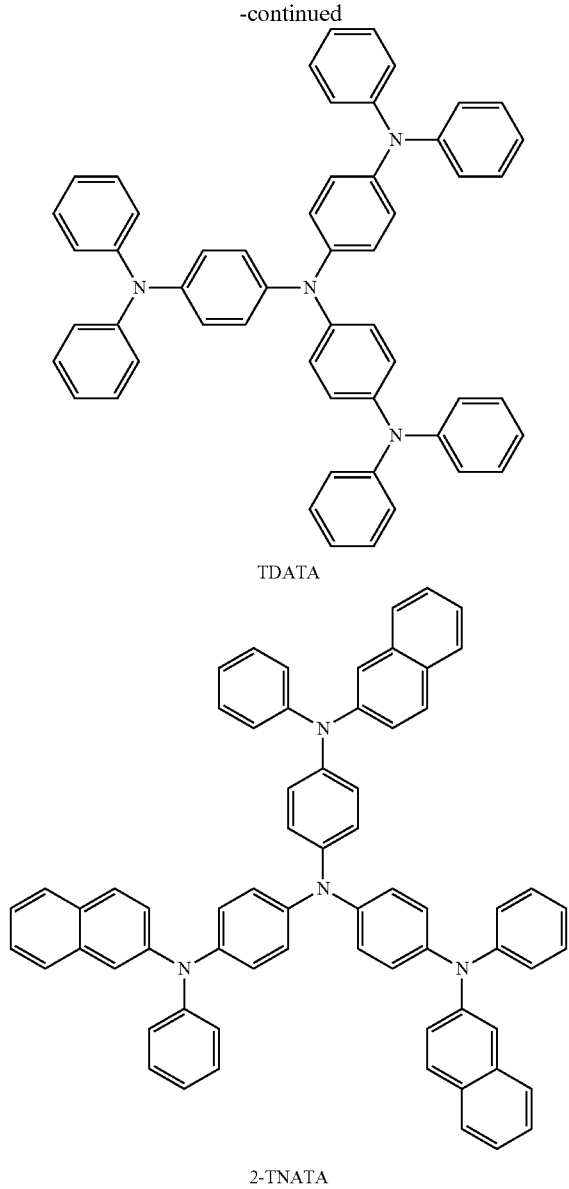

The HIL may have a thickness of about 100 Å to about 10000 Å, for example, a thickness of about 100 Å to about 1000 Å. When the thickness of the HIL is within these ranges, the HIL may have good hole injection characteristics without an increase in driving voltage.

Next, the HTL may be formed on the HIL using various methods, for example, vacuum deposition, spin coating, casting, LB deposition, or the like. When the HTL is fanned using vacuum deposition or spin coating, the deposition or coating conditions may be similar to those used to form the HIL, though the deposition or coating conditions may vary according to the material that is used to form the HTL.

Alternatively, known HTL materials may be used. Examples of such HTL materials include, but are not limited to, carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD), or the like.

The HTL may have a thickness of about 50 Å to about 1000 Å, for example, a thickness of about 100 Å to about 600 Å. When the thickness of the HTL is within these ranges, the HTL may have good hole transport characteristics without a substantial increase in driving voltage.

Next, the EML may be formed on the HTL using various methods, for example, vacuum deposition, spin coating, casting, LB deposition, or the like. When the EML is formed using vacuum deposition or spin coating, the deposition or coating conditions may be similar to those used to form the HIL, though the deposition or coating conditions may vary according to the material that is used to form the EML.

The EML may include the heterocyclic compound of Formula 1 or Formula 2 described above. For example, the heterocyclic compound of Formula 1 or Formula 2 may be used as a host or a dopant. The EML may be formed using a variety of known light-emitting materials, in addition to the heterocyclic compound of Formula 1 or Formula 2. Alternatively, the EML may also be formed using a known host and a dopant. Dopants that may be used to form the EML may include either a fluorescent dopant or a phosphorescent dopant, which are widely known in the art.

Examples of the host may include, but are not limited to, Alq3 4,4'-N,N'-dicarbazole-biphenyl (CPB), 9,10-di(naphthalen-2-yl)anthracene (ADN), and distyrylarylene (DSA).

Examples of red dopants include, but are not limited to, platinum(II) octaethylporphyrin (PtOEP), Ir(piq)$_3$, Btp$_2$Ir (acac), and DCJTB.

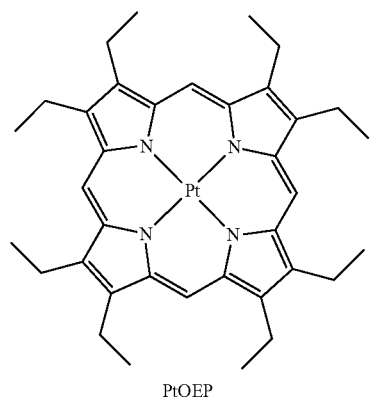

PtOEP

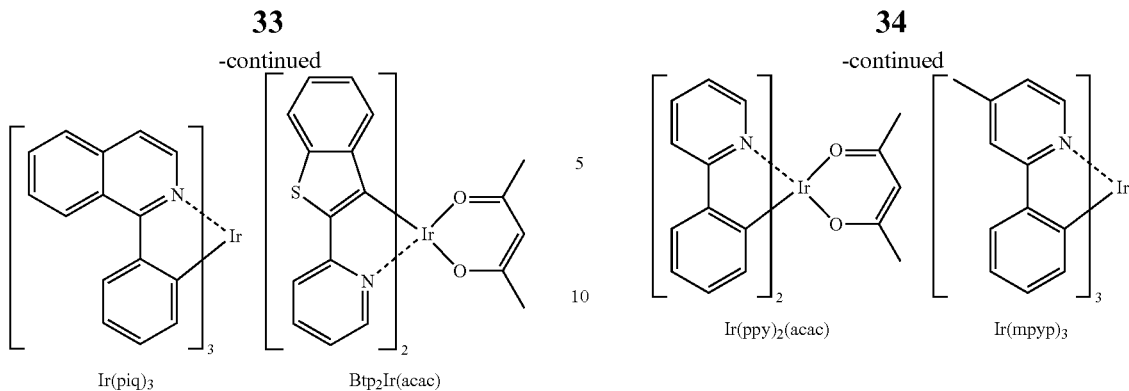
Examples of green dopants include, but are not limited to, Ir(ppy)3 (where "ppy" denotes phenylpyridine), Ir(ppy)2(acac), Ir(mpyp)3, and C545T.
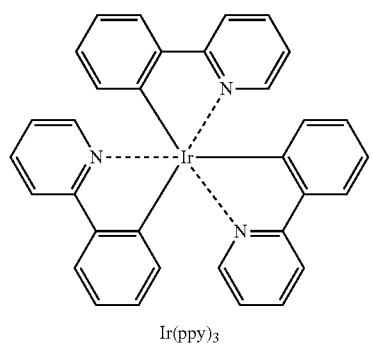
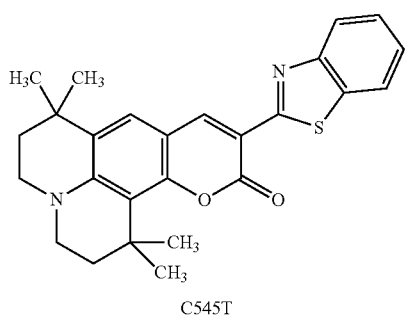
Examples of blue dopants include, but are not limited to, F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl phenylene (TBP).
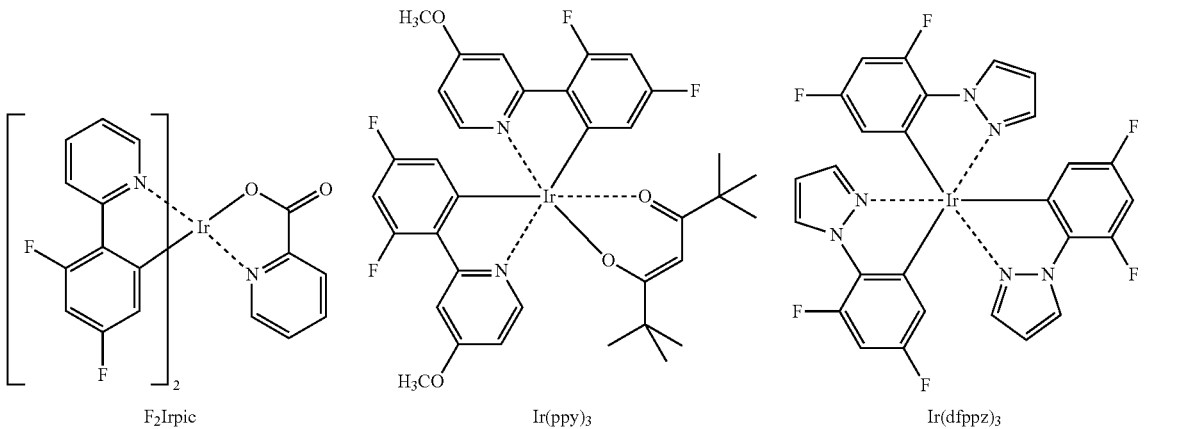
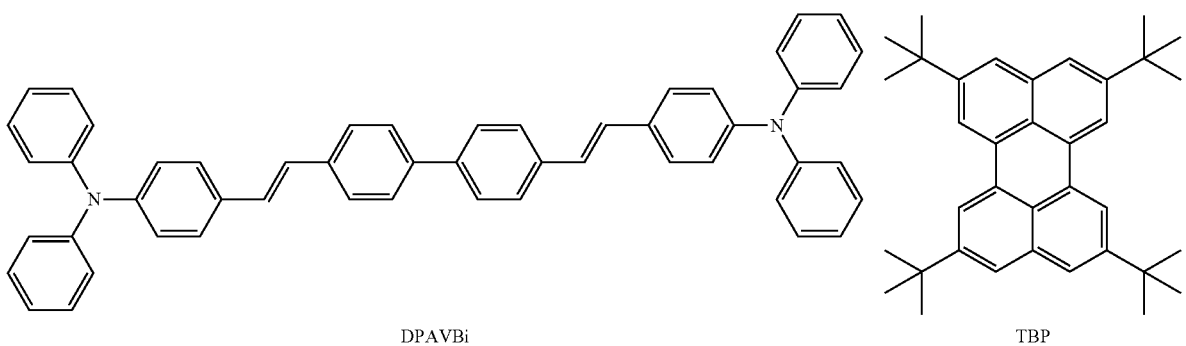

The amount of the dopant may be in a range of about 0.1 to about 20 parts by weight, or about 0.5 to about 12 parts by weight, based on 100 parts by weight of the EML material (which is equivalent to the total weight of the host and the dopant). When the amount of the dopant is within these ranges, concentration quenching may be substantially prevented.

The EML may have a thickness of about 100 Å to about 1,000 Å, for example, about 200 Å to about 600 Å. When the thickness of the EML is within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may comprise any material commonly used to form a HBL, without limitation. Examples of such HBL materials include, but are not limited to, oxadiazole derivatives, triazole derivatives, phenanthroline derivatives, BAlq, and BCP.

The HBL may have a thickness of about 50 Å to about 1,000 Å, for example, about 100 Å to about 300 Å. When the thickness of the HBL is within these ranges, the HBL may have good hole blocking characteristics without a substantial increase in driving voltage.

Next, the ETL is formed on the EML (or HBL) using various methods, for example, vacuum deposition, spin coating, casting, or the like. When the ETL is formed using vacuum deposition or spin coating, the deposition or coating conditions may be similar to those used to form the HIL, though the deposition or coating conditions may vary according to the material used to form the ETL.

The ETL material may include the heterocyclic compound of Formula 1 or Formula 2 described above. Alternatively, the ETL may comprise any known material. Examples of the ETL material include, but are not limited to, quinoline derivatives, such as tris(8-quinolinolate)aluminum (Alq3), TAZ, and BAlq.

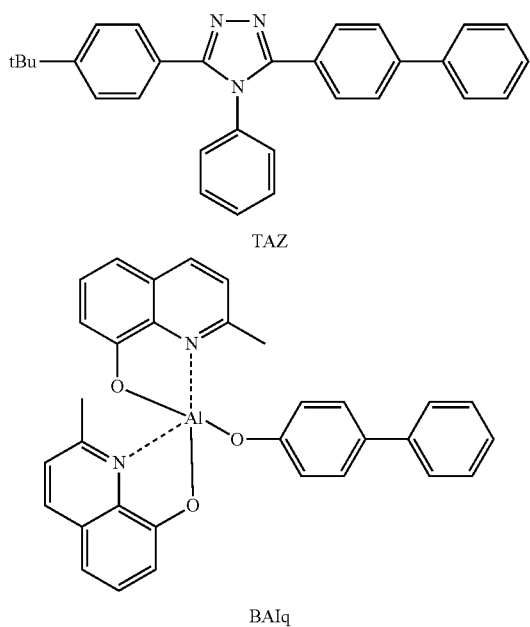

TAZ

BAlq

The ETL may have a thickness of about 100 Å to about 1,000 Å, for example, about 100 Å to about 500 Å. When the thickness of the ETL is within these ranges, the ETL may have good electron transport characteristics without a substantial increase in driving voltage.

In addition, the EIL, which facilitates injection of electrons from the cathode, may be formed on the ETL.

An EIL material may include the heterocyclic compound of Formula 1 or Formula 2 described above. Alternatively, well-known EIL materials, such as LiF, NaCl, CsF, $Li_2O$, or BaO, may be used to form the EIL. The deposition or coating conditions for forming the EIL may be similar to those applied to form the HIL, though the deposition or coating conditions may vary according to the material that is used to form the EIL.

The EIL may have a thickness of about 1 Å to 100 Å, for example, about 5 Å to about 90 Å. When the thickness of the EIL is within these ranges, the EIL may have good electron injection characteristics without a substantial increase in driving voltage.

The second electrode may be formed on the EIL by using, for example, vacuum deposition, sputtering, or the like. The second electrode may be a cathode or an anode. A second electrode material may include a metal, an alloy, an electrically conductive compound, or mixtures thereof, all of which have low work functions. Examples of such materials include, but are not limited to, lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode comprising a transparent material such as ITO or IZO may be used as the second electrode.

The organic light-emitting device according to embodiments may be included in various types of flat panel display devices, such as in a passive matrix organic light-emitting display device or in an active matrix organic light-emitting display device. For example, when the organic light-emitting device is used in an active matrix organic light-emitting display device, the first electrode disposed on the substrate may function as a pixel electrode and may be electrically connected to a source electrode or drain electrode of a thin-film transistor. Moreover, the organic light-emitting device may also be included in flat panel display devices having double-sided screens.

According to some embodiments, at least one layer of the organic light-emitting device may comprise the heterocyclic compound of Formula 1 or Formula 2 using a deposition method or a wet method of coating a solution of the heterocyclic compound of Formula 1 or Formula 2.

Hereinafter, synthesis examples of Compounds 10, 17, 27, 33 and 42 and examples will be described in detail. However, these examples are presented for illustrative purposes only, and do not limit the scope of the present embodiments.

SYNTHESIS EXAMPLE

Synthesis of Compound 10

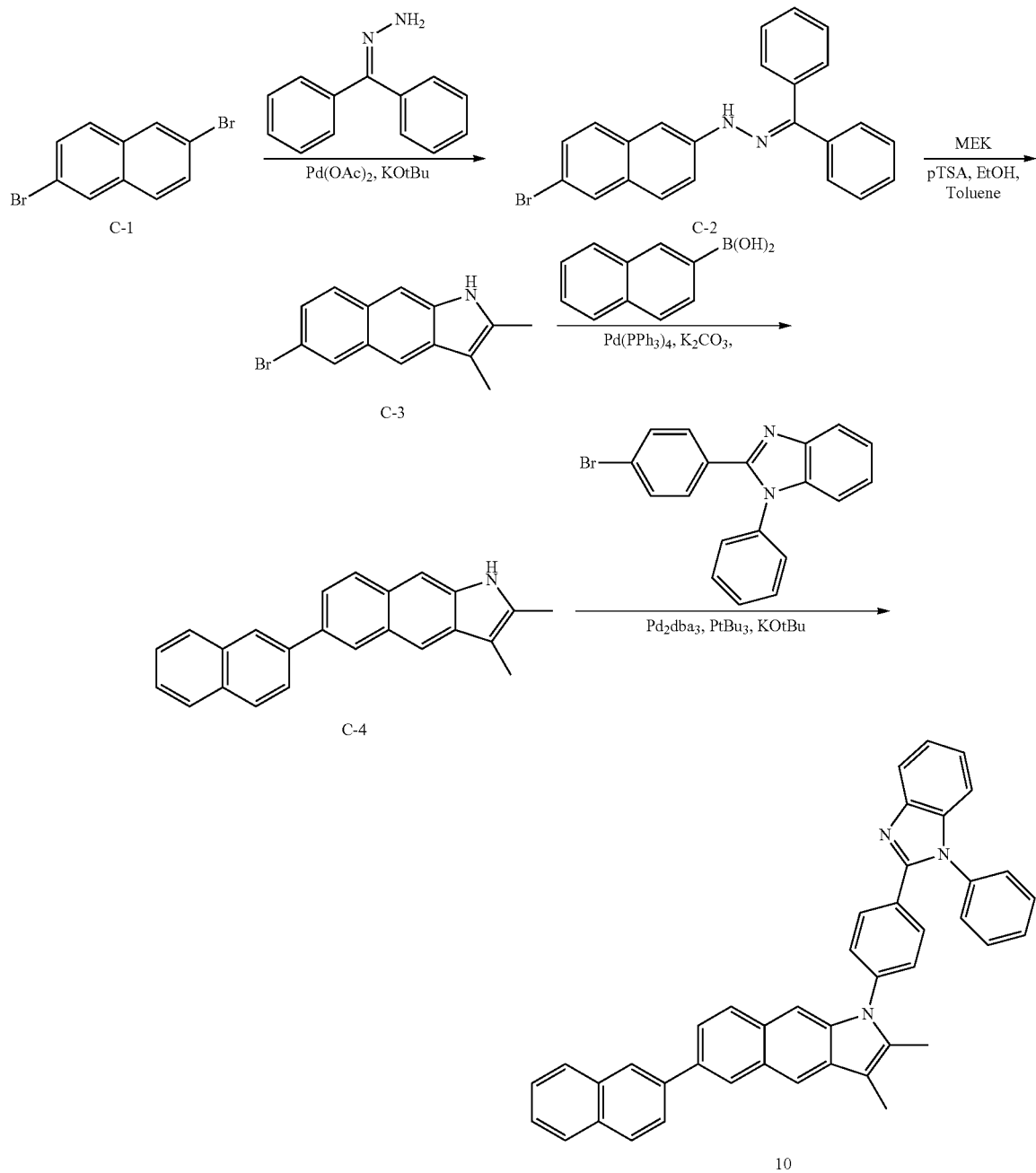

Synthesis of Intermediate C-2

300 mL of toluene was added to a mixture of 28.6 g (100 mmol) of Compound C-1, 9.8 g (50 mmole) of benzophenone hydrazone, 330 mg (3 mol %) of Pd(OAc)$_2$, and 7.3 g (75.0 mmol) of KOt-Bu and then heated at 90° C. in a nitrogen atmosphere for 4 hours. The reaction mixture was cooled to room temperature, and 100 mL of water was further added to the reaction mixture and was extracted twice with 500 mL of methylene chloride. The organic phase was dried, filtered, concentrated, and then separated using column chromatography to obtain 14.4 g of Compound C-2 in yellow solid form with a yield of 72%. The structure of Compound C-2 was identified using high-resolution mass spectrometry (HR-MS). (calc.; 400.0575, found; 400.0564)

Synthesis of Intermediate C-3

100 mL of toluene and 50 mL of ethanol were added to a mixture of 20.1 g (50 mmole) of Compound C-2, 38.0 g (200 mmole) of pTSA.H₂O and 50 mL of methyl ethyl ketone and then heated at 90° C. for 36 hours. The reaction mixture was cooled to room temperature, and 100 mL of water was further added to the reaction mixture and was extracted twice with 200 mL of methylene chloride. The organic phase was dried, filtered, concentrated, and then separated using column chromatography to obtain 10.7 g of Compound C-3 in light-green solid form with a yield of 78%. The structure of Compound C-3 was identified using HR-MS. (calc.; 273.0153, found; 273.0145)

Synthesis of Intermediate C-4

30 mL of water and 100 mL of tetrahydrofuran (THF) were added to a mixture of 7.4 g (30 mmole) of Compound C-3, 2.4 g (33 mmole) of 2-naphthalen-2-yl-2-boronic acid, 1.7 g (5 mol %) of Pd(PPh₃)₄, and 4.8 g (120 mmole) of NaOH and then heated at 70° C. in a nitrogen atmosphere for 12 hours. The reaction mixture was cooled to room temperature, and 50 mL of water was further added to the reaction mixture and was extracted twice with 300 mL of methylene chloride. The organic phase was dried, filtered, concentrated, and then separated using column chromatography to obtain 8.55 g of Compound C-4 in pale-yellow solid form with a yield of 64%. The structure of Compound C-4 was identified using HR-MS. (calc.; 321.1517, found; 321.1508)

Synthesis of Compound 10

100 mL of toluene was added to a mixture of 13.3 g (30.0 mmole) of Compound C-4, 13.6 g (39.0 mmole) of a 2-(4-bromophenyl)-1-phenyl-1H-benzo[d]imidazole, 4.3 g (45.0 mmole) of NaOt-Bu, 1.4 g (1.5 mmole) of Pd₂(dba)₃, and 0.30 g (1.5 mmole) of PtBu₃ and then heated at 90° C. in a nitrogen atmosphere for 6 hours. The reaction mixture was cooled to room temperature, and 30 mL of water was further added to the reaction mixture and was extracted twice with 200 mL of methylene chloride. The organic phase was dried, filtered, concentrated, and then separated using column chromatography to obtain 10.2 g of Compound 10 in light-yellow solid form with a yield of 58%. The structure of Compound 10 was identified using nuclear magnetic resonance (NMR) spectroscopy and HR-MS.

1H-NMR (CDCl3, 400 MHz) δ (ppm); 6.71-6.89 (m, 2H), 7.45-7.98 (m, 23H), 2.35 (s, 3H), 2.31 (s, 3H). 13-C NMR (CDCl3, 100 MHz) δ (ppm); 141.1, 140.5, 140.1, 138.4, 138.1, 136.7, 135.8, 133.2, 133.0, 132.8, 132.1, 130.7, 129.9, 129.2, 128.5, 128.2, 126.5, 126.2, 124.3, 123.6, 123.0 120.9, 120.7, 120.5, 120.0, 116.7, 116.4, 116.0, 114.2, 112.1, 12.5, 8.9.

HRMS (calc.; 589.2518, found; 589.2511)

Synthesis Example

Synthesis of Compound 17

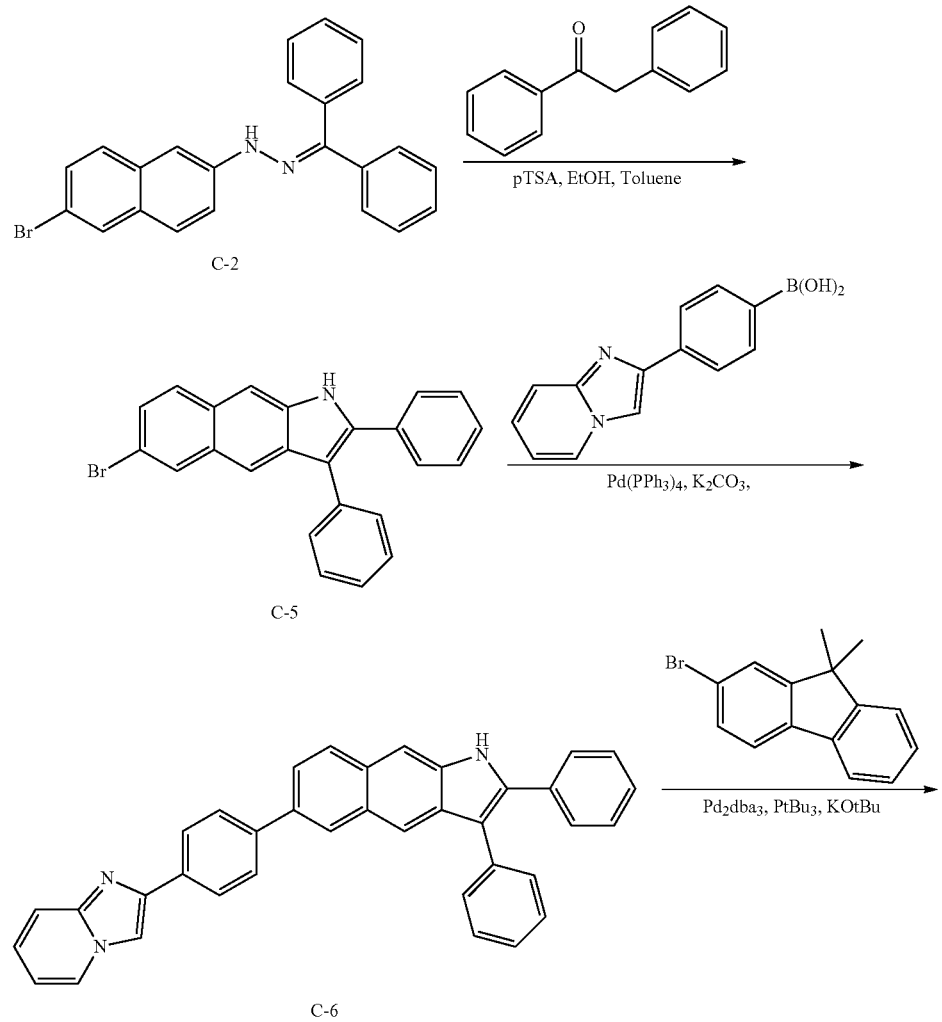

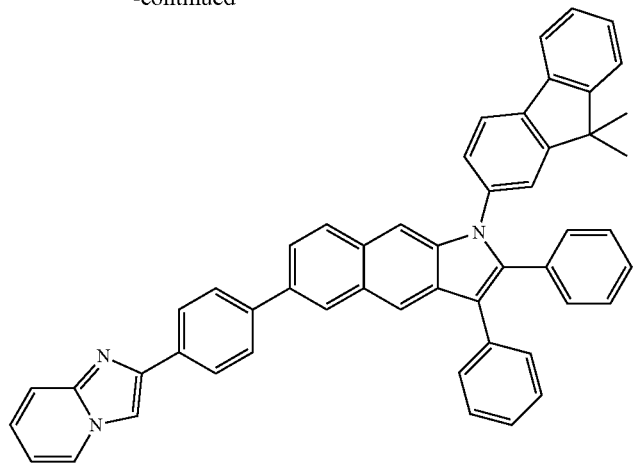

17

Synthesis of Intermediates C-5 and C-6 and Compound 17

11.1 g of Compound C-5 in pale-yellow solid form was synthesized with a yield of 56% in the same manner as used in the synthesis of Compound C-3, except that 19.6 g (100 mmole) of benzyl phenyl ketone was used, instead of methyl ethyl ketone. The structure of Compound C-5 was identified using HR-MS. (calc.; 397.0466, found; 397.0454)

9.9 g of Compound C-6 in pale-yellow solid was synthesized with a yield of 76%, using 11.5 g (30 mmole) of Compound C-5 and 5.3 g (33 mmole) of imidazole boronic acid in the same manner as used in the synthesis of Compound C-4. The structure of Compound C-6 was identified using HR-MS. (calc.; 435.1735, found; 435.1727)

11.6 g of Compound 17 in light-yellow solid was synthesized with a yield of 55%, using 13.0 g (30 mmole) of Compound C-6 and 10.6 g (39 mmole) of bromodimethyl fluorene in the same manner as used in the synthesis of Compound 10. The structure of Compound 10 was identified using HR-MS.

1H-NMR (CDCl3, 400 MHz) δ (ppm); 6.89-7.78 (m, 31H), 1.87 (s, 6H). 13-C NMR (CDCl3, 100 MHz) δ (ppm); 143.2, 142.5, 142.1, 140.4, 140.1, 138.7, 138.8, 138.2, 136.0, 135.8, 135.1, 134.7, 133.9, 133.2, 132.5, 132.2, 131.5, 131.2, 130.3, 129.6, 129.0, 128.6, 128.2, 127.5, 127.0, 125.4, 124.7, 124.1, 123.6, 123.1, 122.1, 121.1, 119.7, 116.7, 116.4, 116.0, 114.2, 112.1, 38.2, 27.5.

HRMS (calc.; 627.2674, found; 627.2662)

Synthesis Example

Synthesis of Compound 27

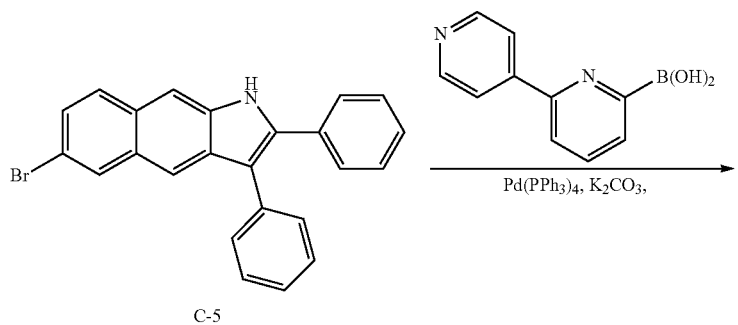

C-5

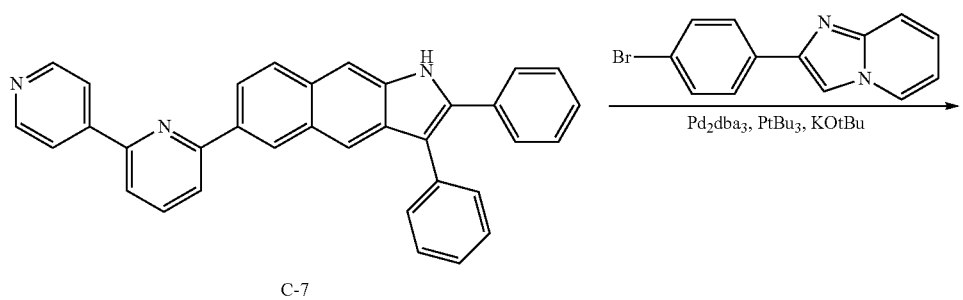

C-7

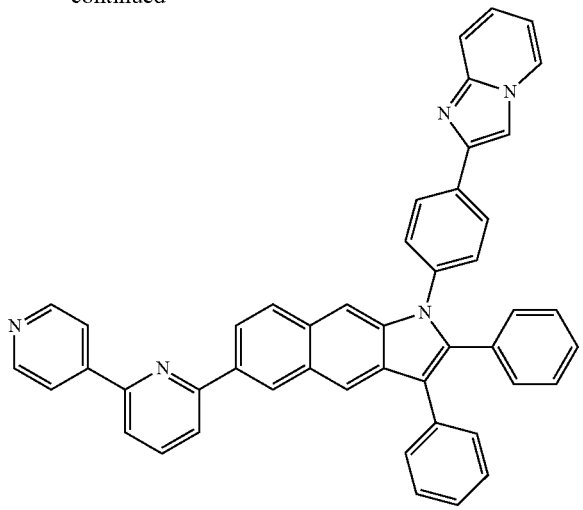

27

Synthesis of Intermediate C-7 and Compound 27

10.1 g of Compound C-7 in pale-yellow solid was synthesized with a yield of 71%, using 11.9 g (30 mmole) of Compound C-5 and 6.6 g (33 mmole) of bipyridyl boronic acid in the same manner as used in the synthesis of Compound C-4. The structure of Compound C-7 was identified using HR-MS. (calc.; 473.1892, found; 473.1881)

8.9 g of Compound 27 in light-yellow solid was synthesized with a yield of 45%, using 14.2 g (30 mmole) of Compound C-7 and 10.6 g (39 mmole) of 2-(4-bromophenyl)H-imidazo[1,2-a]pyridine in the same manner as used in the synthesis of Compound 10. The structure of Compound 27 was identified using NMR spectroscopy and HR-MS.

1H-NMR (CDCl3, 400 MHz) δ (ppm); 6.89-7.02 (m, 2H), 7.24-7.78 (m, 25H), 8.01-8.88 (m, 4H). 13-C NMR (CDCl3, 100 MHz) δ (ppm); 155.2, 154.5, 152.1, 150.4, 140.1, 139.7, 139.1, 138.6, 136.5, 135.1, 134.1, 134.0, 133.6, 133.2, 132.5, 132.2, 131.5, 131.2, 131.5, 130.3, 129.6, 129.0, 128.5, 128.2, 127.4, 127.0, 126.4, 125.7, 125.1, 124.1, 123.7, 123.3, 122.8, 122,0, 121.5, 119.9, 116.6, 116.4, 116.0, 114.2, 112.5.
HRMS (calc.; 665.2579, found; 665.2571)

Synthesis Example

Synthesis of Compound 33

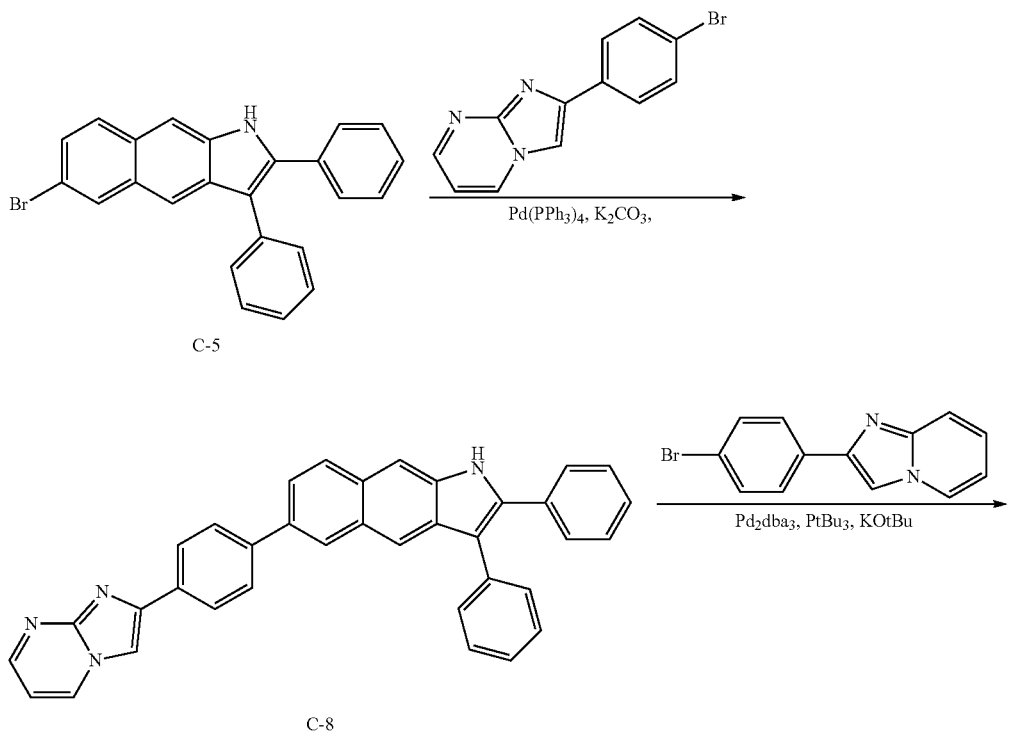

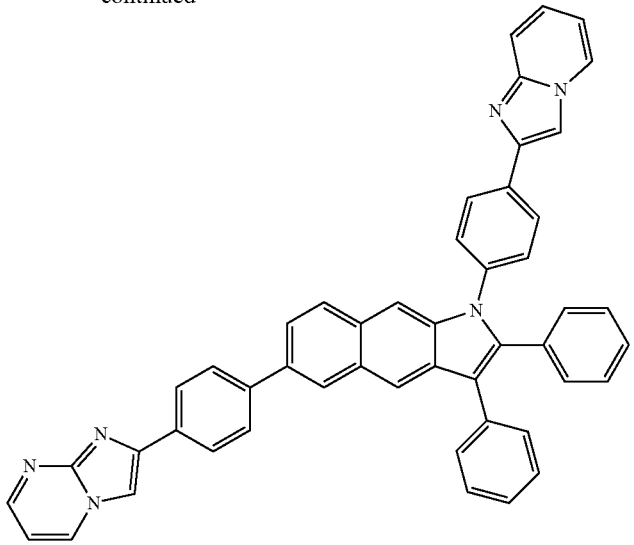

33

9.9 g of Compound C-8 in pale-yellow solid was synthesized with a yield of 65%, using 11.9 g (30 mmole) of Compound C-5 and 9.0 g (33 mmole) of 4-imidazopyrimidyl boronic acid in the same manner as used in the synthesis of Compound C-4. The structure of Compound C-8 was identified using HR-MS. (calc.; 512.2001, found; 512.1992)

10.9 g of Compound 33 in light-yellow solid was synthesized with a yield of 55%, using 14.2 g (30 mmole) of Compound C-8 and 10.6 g (39 mmole) of 2-(4-bromophenyl)H-imidazo[1,2-a]pyridine in the same manner as used in the synthesis of Compound 10. The structure of Compound 33 was identified using NMR spectroscopy and HR-MS.

1H-NMR (CDCl3, 400 MHz) δ (ppm); 6.79-7.08 (m, 2H), 7.21-7.74 (m, 27H), 8.51-8.84 (m, 2H). 13-C NMR (CDCl3, 100 MHz) δ (ppm); 156.2, 154.6, 153.1, 150.6, 143.1, 141.7, 140.1, 139.6, 138.5, 138.1, 137.1, 136.7, 135.6, 135.2, 134.6, 134.2, 131.5, 131.2, 131.0, 130.7, 129.6, 129.1, 128.5, 128.2, 127.4, 127.0, 126.5, 125.7, 125.1, 124.8, 123.7, 123.2, 122.8, 122,2, 121.5, 119.0, 116.6, 116.4, 116.0, 114.2.
HRMS (calc.; 704.2688, found; 704.2680)

Synthesis Example

Synthesis of Compound 42

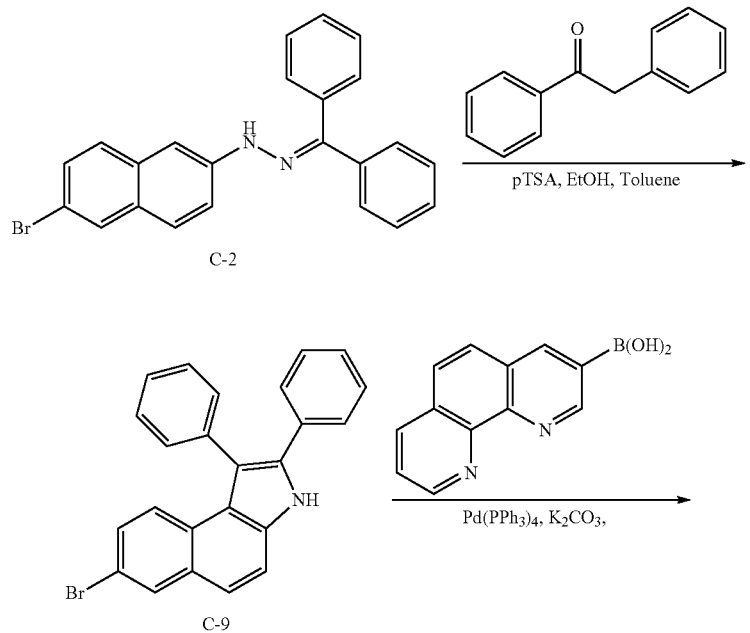

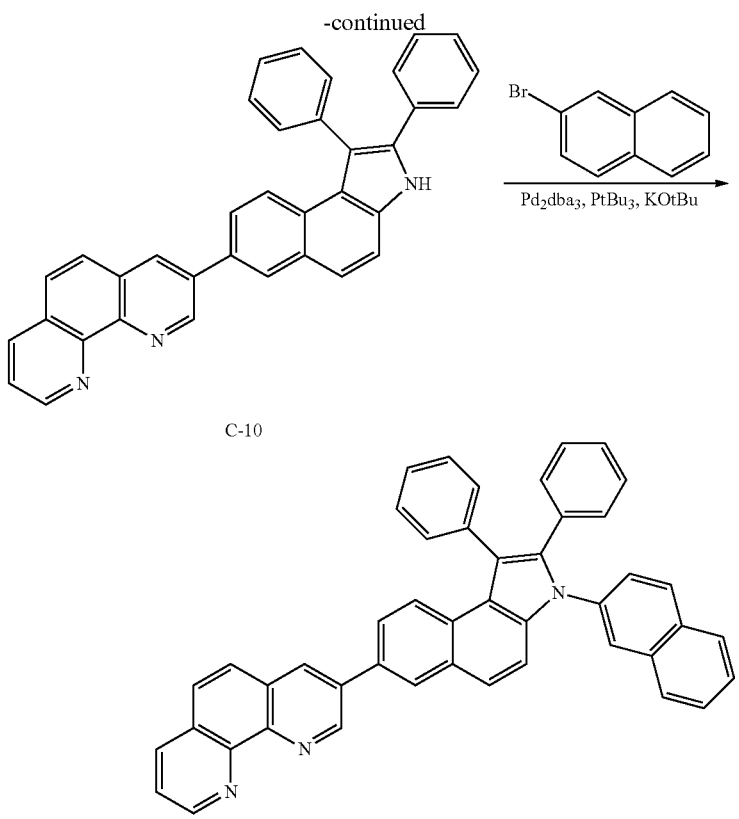

6.77 g of Compound C-9 in pale-yellow solid form was synthesized with a yield of 34% in the same manner as used in the synthesis of Compound C-3, except that 19.6 g (100 mmole) of benzyl phenyl ketone was used, instead of methyethylketone. The structure of Compound C-9 was identified using HR-MS. (calc.; 397.0466, found; 397.0456)

9.2 g of Compound C-10 in pale-yellow solid was synthesized with a yield of 62%, using 11.9 g (30 mmole) of Compound C-9 and 7.39 g (33 mmole) of phenanthroline boronic acid in the same manner as used in the synthesis of Compound C-4. The structure of Compound C-10 was identified using HR-MS. (calc.; 497.1892, found; 497.1884)

12.1 g of Compound 42 in light-yellow solid was synthesized with a yield of 65%, using 14.9 g (30 mmole) of Compound C-10 and 6.79 g (39 mmole) of bromonaphthalene in the same manner as used in the synthesis of Compound 10. The structure of Compound 42 was identified using NMR spectroscopy and HR-MS.

1H-NMR (CDCl3, 400 MHz) δ (ppm); 8.56-8.87 (m, 2H), 7.87-8.21 (m, 4H), 7.21-7.76 (m, 23H). 13-C NMR (CDCl3, 100 MHz) δ (ppm); 158.4, 149.5, 149.1, 146.4, 145.1, 144.2, 140.5, 138.7, 138.2, 136.0, 135.8, 134.9, 133.3, 132.5, 132.2, 131.5, 130.3, 129.6, 129.0, 127.5, 125.2, 123.7, 123.1, 122.6, 122.1, 120,1, 119.7, 116.7, 116.4, 116.0, 114.2, 112,1, HRMS (calc.; 704.2688, found; 704.2680)

Example 1

An anode was prepared by cutting a Corning 15 Ωcm² (1200 Å) ITO glass substrate to a size of 50 mm×50 mm×0.7 mm, ultrasonically cleaning the glass substrate using isopropyl alcohol and pure water for 5 minutes each, and then irradiating UV light for 30 minutes and exposing to ozone to clean. Then, the anode was loaded into a vacuum deposition apparatus.

Then, 2-TNATA (which is a HIL material) was vacuum-deposited on the glass substrate to form a HIL having a thickness of about 600 Å. Then, 4,4'-bis[N-(1-naphthyl)-N-phenylamino]biphenyl (NPB) (which is a hole transporting compound) was vacuum-deposited on the HIL to form a HTL having a thickness of about 300 Å.

Then, a green fluorescent host (Alq3) and a green fluorescent dopant (C545T) were simultaneously deposited in a weight ratio of 98:2 on the HTL, to form an EML having a thickness of about 300 Å.

Then, Compound 10 was deposited on the EML to form an ETL having a thickness of about 300 Å, and then LiF (which is halogenated alkali metal) was deposited on the ETL to form an EIL having a thickness of about 10 Å. Then, Al was vacuum-deposited on the EIL to a thickness of about 3000 Å to form a LiF/Al electrode (cathode), thereby completing the manufacture of an organic light-emitting device.

The organic light-emitting device had a driving voltage of 5.87 V at a current density of 50 mA/cm², a high luminosity of 8,134 cd/m², color coordinates of (0.310, 0.644), and a luminescent efficiency of 16.27 cd/A.

Example 2

An organic light-emitting device was manufactured in the same manner as in Example 1, except that Compound 17 was used instead of Compound 10 to form the ETL.

The organic light-emitting device had a driving voltage of 6.17 V at a current density of 50 mA/cm², a high luminosity of 8,384 cd/m², color coordinates of (0.310, 0.643), and a luminescent efficiency of 16.77 cd/A.

Example 3

An organic light-emitting device was manufactured in the same manner as in Example 1, except that Compound 27 was used instead of Compound 10 to form the ETL.

The organic light-emitting device had a driving voltage of 5.67 V at a current density of 50 mA/cm², a high luminosity of 8,796 cd/m², color coordinates of (0.309, 0.642), and a luminescent efficiency of 17.59 cd/A.

Example 4

An organic light-emitting device was manufactured in the same manner as in Example 1, except that Compound 33 was used instead of Compound 10 to form the ETL.

The organic light-emitting device had a driving voltage of 5.47V at a current density of 50 mA/cm², a high luminosity of 8,904 cd/m², color coordinates of (0.309, 0.643), and a luminescent efficiency of 17.8 cd/A.

Example 5

An organic light-emitting device was manufactured in the same manner as in Example 1, except that Compound 42 was used instead of Compound 10 to form the ETL.

The organic light-emitting device had a driving voltage of 5.83 V at a current density of 50 mA/cm², a high luminosity of 8,064 cd/m², color coordinates of (0.310, 0.642), and a luminescent efficiency of 16.13 cd/A.

Comparative Example 1

An organic light-emitting device was manufactured in the same manner as in Example 1, except that Alq3 was used, instead of Compound 10, to form the ETL.

The organic light-emitting device had a driving voltage of 7.45 V at a current density of 50 mA/cm², a high luminosity of 6,102 cd/m², color coordinates of (0.309, 0.642), which is almost the same as that of the organic light-emitting device of Example 1, and a luminescent efficiency of 12.2 cd/A.

The organic light-emitting devices including the heterocyclic compounds of Formula 1 or Formula 2 as an ETL material had a driving voltage that was lower by 1V or greater than the organic light-emitting device manufactured using Alq3, and thus had higher efficiency and good I-V-L characteristics. In particular, lifetime characteristics were markedly improved by 100% or greater in the organic light-emitting devices of Examples 1 through 5, as compared with the organic light-emitting device of Comparative Example 1.

As described above, novel heterocyclic compounds according to the one or more of the above embodiments have good electrical characteristics, good charge transporting capabilities and good emission characteristics, and may be used to prevent crystallization due to high glass transition temperatures ($T_g$). The heterocyclic compounds may also be used as electron transporting materials for most color-fluorescent and phosphorescent devices, such as red, green, blue, and white fluorescent and phosphorescent devices, or as red, green, blue or white-light emitting materials. Thus, an organic light-emitting device with high-efficiency, low-driving voltage, high luminance and long lifespan may be manufactured using the heterocyclic compounds.

While the present embodiments have been particularly shown and described with reference to example embodiments thereof, it will be understood by those of ordinary skill in the art that various changes in form and details may be made therein without departing from the spirit and scope of the present embodiments as defined by the following claims.

What is claimed is:
1. An organic light-emitting device comprising:
a first electrode;
a second electrode; and
an organic layer between the first electrode and the second electrode,
the organic layer comprising a first layer including a heterocyclic compound represented by Formula 1 below:

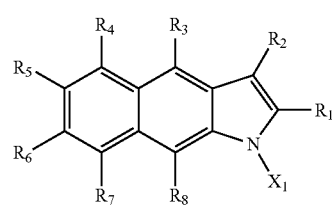

Formula 1 wherein $X_1$ is a substituted or unsubstituted $C_1$-$C_{50}$ alkyl group, a substituted or unsubstituted $C_3$-$C_{50}$ cycloalkyl group, a substituted or unsubstituted $C_5$-$C_{50}$ arylthio group, a substituted or unsubstituted $C_5$-$C_{60}$ aryl group, a substituted amino group with a $C_5$-$C_{60}$ aryl group, a substituted or unsubstituted $C_3$-$C_{60}$ heteroaryl group, or a substituted or unsubstituted $C_6$-$C_{60}$ condensed polycyclic group; and $R_1$ and $R_2$ are each independently a hydrogen atom, a heavy hydrogen atom, a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a substituted or

TABLE 1

| | ETL material | Driving voltage (V) | Current density (mA/cm²) | Luminance (cd/m²) | Luminescent efficiency (cd/A) | Color coordinates | Half life-span (hr @100 mA/cm²) |
|---|---|---|---|---|---|---|---|
| Example 1 | Compound 10 | 5.87 | 50 | 8134 | 16.27 | (0.310, 0.644) | 489 hr |
| Example 2 | Compound 17 | 6.17 | 50 | 8384 | 16.77 | (0.310, 0.643) | 510 hr |
| Example 3 | Compound 27 | 5.67 | 50 | 8796 | 17.59 | (0.309, 0.642) | 523 hr |
| Example 4 | Compound 33 | 5.47 | 50 | 8904 | 17.8 | (0.309, 0.643) | 558 hr |
| Example 5 | Compound 42 | 5.83 | 50 | 8064 | 16.13 | (0.310, 0.642) | 482 hr |
| Comparative Example 1 | Alq3 | 7.45 | 50 | 6102 | 12.2 | (0.309, 0.642) | 237 hr | unsubstituted $C_5$-$C_{60}$ aryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group, $R_5$ is selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a unsubstituted $C_5$-$C_{50}$ arylamine group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group or a halogen group; a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group or a halogen group; or a substituted $C_5$-$C_{50}$ arylamine group which is substituted with a $C_1$-$C_5$ alkyl group, a $C_1$-$C_5$ alkoxy group, a cyano group, an amine group, a phenoxy group, a phenyl group and a halogen group, $R_3$, $R_4$, and $R_6$-$R_8$ are each independently a hydrogen atom or a heavy hydrogen atom.

2. An organic light-emitting device comprising:
a first electrode;
a second electrode; and
an organic layer between the first electrode and the second electrode,
the organic layer comprising a first layer including a heterocyclic compound represented by Formula 2 below:

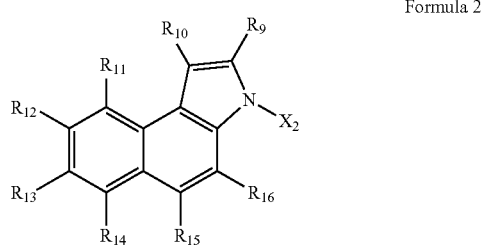

Formula 2 wherein $X_2$ is a substituted or unsubstituted $C_1$-$C_{50}$ alkyl group, a substituted or unsubstituted $C_3$-$C_{50}$ cycloalkyl group, a substituted or unsubstituted $C_5$-$C_{50}$ arylthio group, a substituted or unsubstituted $C_5$-$C_{60}$ aryl group, a substituted amino group with a $C_5$-$C_{60}$ aryl group, a substituted or unsubstituted $C_3$-$C_{60}$ heteroaryl group, or a substituted or unsubstituted $C_6$-$C_{60}$ condensed polycyclic group; and $R_9$ and $R_{10}$ are each independently a hydrogen atom, a heavy hydrogen atom, a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a substituted or unsubstituted $C_5$-$C_{60}$ aryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group, $R_{11}$, $R_{12}$, and $R_{14}$-$R_{16}$ are each independently a hydrogen atom or a heavy hydrogen atom;

$R_{13}$ is selected from the group consisting of a phenyl group, a naphthyl group, a biphenyl group, a terphenyl group, an anthracenyl group, a fluorenyl group, and a pyrenyl group; an unsubstituted $C_{3\text{-}C60}$ heteroaryl group; a unsubstituted $C_5$-$C_{50}$ arylamine group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group or a halogen group; a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group or a halogen group; or a substituted $C_5$-$C_{50}$ arylamine group which is substituted with a $C_1$-$C_5$ alkyl group, a $C_1$-$C_5$ alkoxy group, a cyano group, an amine group, a phenoxy group, a phenyl group and a halogen group.

3. The organic light-emitting device of claim 1, wherein $R_1$ and $R_2$ are each independently a substituted or unsubstituted $C_6$-$C_{60}$ aryl group.

4. The organic light-emitting device of claim 2, wherein $R_9$ and $R_{10}$ are each independently a substituted or unsubstituted $C_6$-$C_{60}$ aryl group.

5. The organic light-emitting device of claim 1, wherein at least one of $R_1$, $R_2$ or $R_5$ is a unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a unsubstituted $C_5$-$C_{50}$ arylamine group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group or a halogen group; a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group or a halogen group; or a substituted $C_5$-$C_{50}$ arylamine group which is substituted with a $C_1$-$C_5$ alkyl group, a $C_1$-$C_5$ alkoxy group, a cyano group, an amine group, a phenoxy group, a phenyl group and a halogen group.

6. The organic light-emitting device of claim 2, wherein at least one of $R_9$, $R_{10}$ or $R_{13}$ is a unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a unsubstituted $C_5$-$C_{50}$ arylamine group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group or a halogen group; a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group or a halogen group; or a substituted $C_5$-$C_{50}$ arylamine group which is substituted with a $C_1$-$C_5$ alkyl group, a $C_1$-$C_5$ alkoxy group, a cyano group, an amine group, a phenoxy group, a phenyl group and a halogen group.

7. The organic light-emitting device of claim 1, wherein $X_1$ is a unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group, a halogen group, or a $C_3$-$C_{10}$ heteroaryl group; or a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group, a halogen group or a $C_3$-$C_{10}$ heteroaryl group.

8. The organic light-emitting device of claim 2, wherein $X_2$ is a unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which are substituted with a $C_1$-$C_5$ alkyl group, a $C_1$-$C_5$ alkoxy group, a cyano group, an amine group, a phenoxy group, a phenyl group, a halogen group, or a $C_3$-$C_{10}$ heteroaryl group; or a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group, a halogen group or a $C_3$-$C_{10}$ heteroaryl group.

9. The organic light-emitting device of claim 1, wherein $R_1$ and $R_2$, are each independently a methyl group or a phenyl group.

10. The organic light-emitting device of claim 2, wherein $R_9$ and $R_{10}$ are each independently a methyl group or a phenyl group.

11. The organic light-emitting device of claim 1, comprising one of the compounds below:

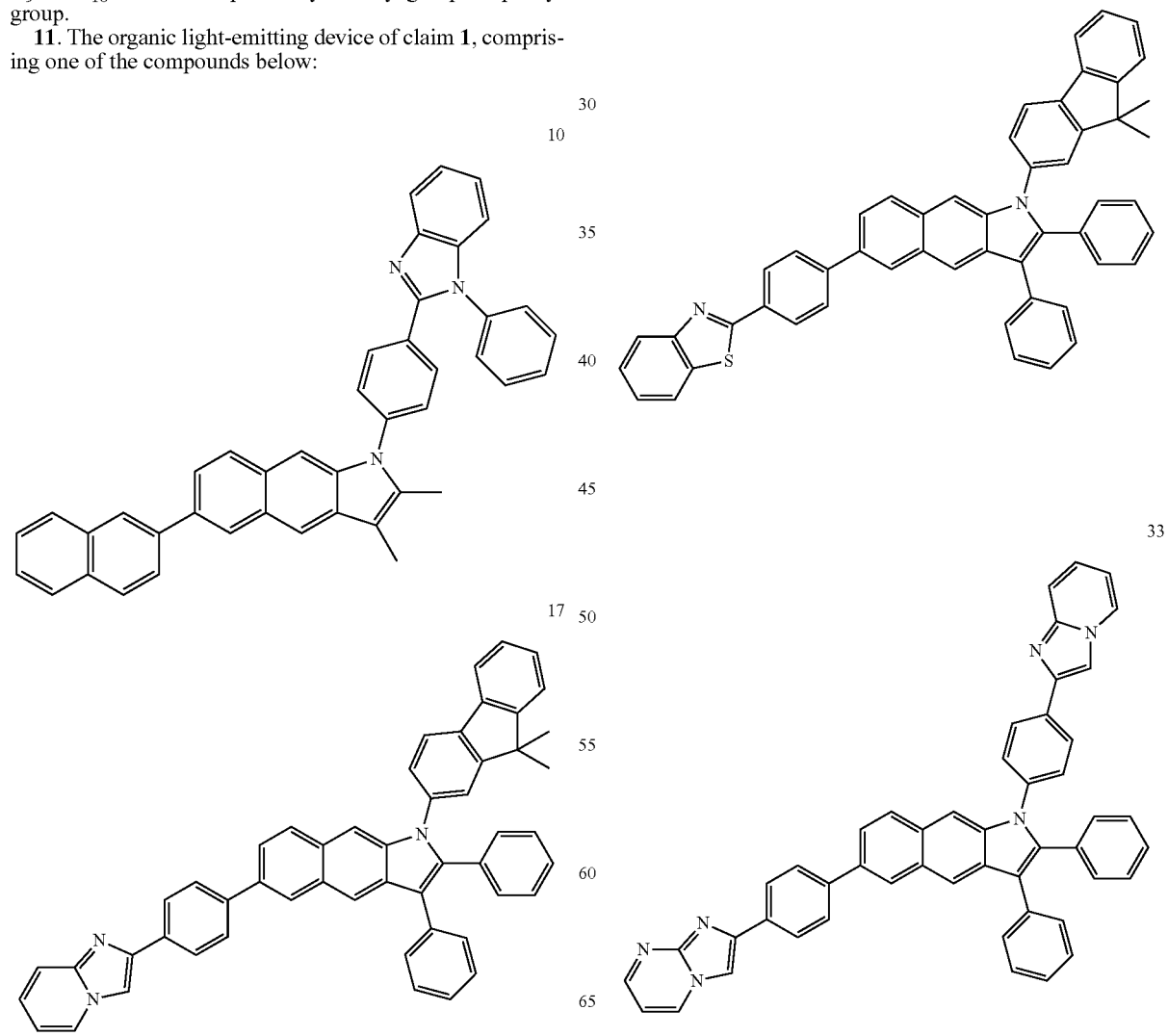

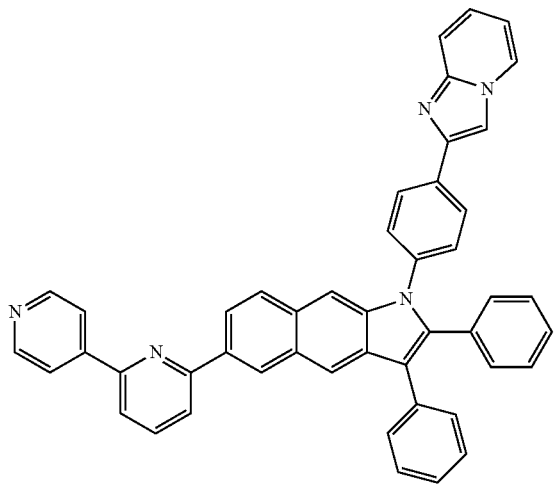

12. The organic light-emitting device of claim 2, comprising one of the compounds below:
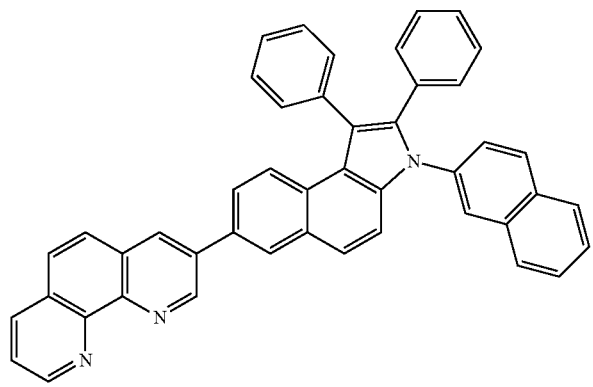
42
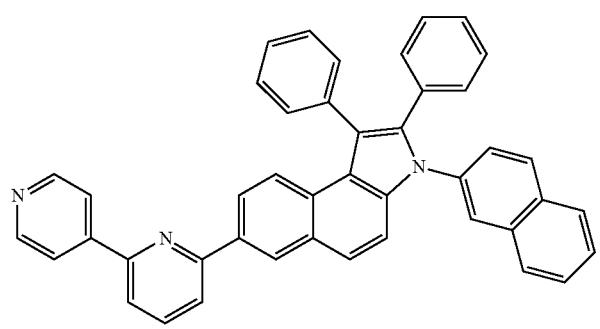
38
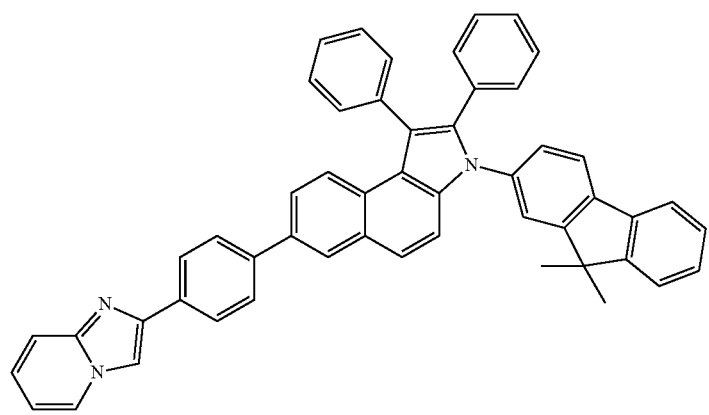
40
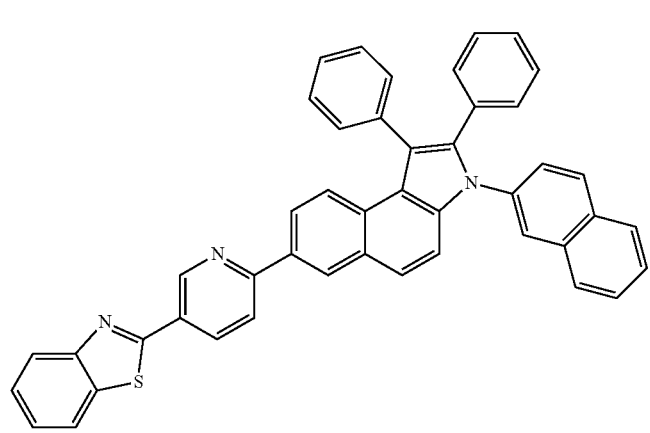
45

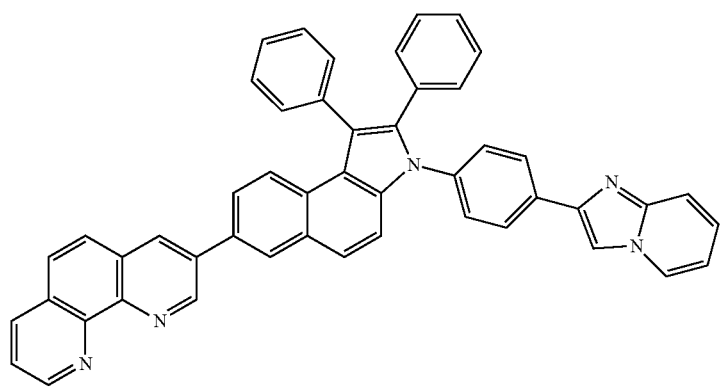

52

13. The organic light-emitting device of claim 1, wherein the first layer comprises an electron injection layer, an electron transport layer a single film having both an electron injection function and an electron transport function, or an emission layer.

14. The organic light-emitting device of claim 2, wherein the first layer comprises an electron injection layer, an electron transport layer a single film having both an electron injection function and an electron transport function, or an emission layer.

15. The organic light-emitting device of claim 1, wherein the first layer comprises an emission layer, and the heterocyclic compound is used as a host or dopant for a fluorescent or phosphorescent device.

16. The organic light-emitting device of claim 2, wherein the first layer comprises an emission layer, and the heterocyclic compound is used as a host or dopant for a fluorescent or phosphorescent device.

17. The organic light-emitting device of claim 1, wherein the first layer comprises at least one of an emission layer, an electron injection layer or an electron transport layer, and wherein the emission layer comprises an anthracene compound, an arylamine compound, or a styryl compound.

18. The organic light-emitting device of claim 2, wherein the first layer comprises an emission layer, an electron injection layer or an electron transport layer, and the emission layer comprises an anthracene compound, an arylamine compound, or a styryl compound.

19. The organic light-emitting device of claim 1, wherein the first layer comprises at least of one of an emission layer, an electron injection layer or an electron transport layer, and wherein the emission layer comprises a red emission layer, a green emission layer, a blue emission layer or a white emission layer that comprises a phosphorescent compound.

20. The organic light-emitting device of claim 2, wherein the first layer comprises an emission layer, an electron injection layer or an electron transport layer, and the emission layer comprises a red emission layer, a green emission layer, a blue emission layer or a white emission layer that comprises a phosphorescent compound.

21. The organic light-emitting device of claim 1, wherein the organic layer further comprises at least one layer selected from the group consisting of a hole injection layer, a hole transport layer, a functional layer having both hole injection and transport functions, an electron blocking layer, an emission layer, a hole blocking layer, an electron transport layer, an electron injection layer and a combination of at least two of these layers.

22. The organic light-emitting device of claim 21, wherein at least one of the hole injection layer, the hole transport layer, and the functional layer having both hole injection and transport functions further comprises a charge-generating material.

23. The organic light-emitting device of claim 21, wherein the electron transport layer comprises an electron transporting organic material and a metal-containing material.

24. The organic light-emitting device of claim 23, wherein the metal-containing material comprises a lithium complex.

25. The organic light-emitting device of claim 2, wherein the organic layer further comprises at least one layer selected from the group consisting of a hole injection layer, a hole transport layer, a functional layer having both hole injection and transport functions, an electron blocking layer, an emission layer, a hole blocking layer, an electron transport layer, an electron injection layer and a combination of at least two of these layers.

26. The organic light-emitting device of claim 25, wherein at least one of the hole injection layer, the hole transport layer, and the functional layer having both hole injection and transport functions further comprises a charge-generating material.

27. The organic light-emitting device of claim 25, wherein the electron transport layer comprises an electron transporting organic material and a metal-containing material.

28. The organic light-emitting device of claim 27, wherein the metal-containing material comprises a lithium complex.

29. The organic light-emitting device of claim 21, having a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport structure layer/electron injection layer/second electrode structure.

30. The organic light-emitting device of claim 25, having a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport structure layer/electron injection layer/second electrode structure.

31. An organic light-emitting device comprising:
a first electrode;
a second electrode; and
an organic layer between the first electrode and the second electrode, wherein the organic layer comprises at least one layer comprising the heterocyclic compound of claim 1, the at least one layer being formed using a wet process.

32. An organic light-emitting device comprising:
a first electrode;
a second electrode; and
an organic layer between the first electrode and the second electrode, wherein the organic layer comprises at least one layer comprising the heterocyclic compound of claim 2, the at least one layer being formed using a wet process.

33. A flat panel display device comprising the organic light-emitting device of claim 1, wherein the first electrode of the organic light-emitting device is electrically connected to a source electrode or a drain electrode of a thin-film transistor.

34. A flat panel display device comprising the organic light-emitting device of claim 2, wherein the first electrode of the organic light-emitting device is electrically connected to a source electrode or a drain electrode of a thin-film transistor.

* * * * *